US010942140B2

(12) United States Patent
Haick et al.

(10) Patent No.: US 10,942,140 B2
(45) Date of Patent: *Mar. 9, 2021

(54) MORPHOLOGY ENGINEERING OF CONDUCTIVE METALLIC NANOPARTICLES CAPPED WITH AN ORGANIC COATING

(71) Applicant: Technion R&D Foundation Ltd., Technion (IL)

(72) Inventors: Hossam Haick, Haifa (IL); Meital Segev-Bar, Haifa (IL); Gregory Shuster, Ramat Yishai (IL); Sagi Gliksman, Ramat Yishai (IL)

(73) Assignee: Technion R&D Foundation Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/861,288

(22) Filed: Apr. 29, 2020

(65) Prior Publication Data

US 2020/0284743 A1    Sep. 10, 2020

Related U.S. Application Data

(62) Division of application No. 13/733,615, filed on Jan. 3, 2013, now Pat. No. 10,663,420.

(Continued)

(51) Int. Cl.
*G01N 27/00* (2006.01)
*B82Y 15/00* (2011.01)
(Continued)

(52) U.S. Cl.
CPC .......... *G01N 27/121* (2013.01); *B82Y 15/00* (2013.01); *G01N 27/127* (2013.01); *G01N 27/223* (2013.01); *G01N 33/0031* (2013.01)

(58) Field of Classification Search
CPC ......... G01N 2015/0038; G01N 27/127; G01N 27/4146; G01N 27/121; G01N 27/223;
(Continued)

(56) References Cited

U.S. PATENT DOCUMENTS 6,458,327 B1   10/2002   Vossmeyer
6,773,926 B1    8/2004   Freund
(Continued)

FOREIGN PATENT DOCUMENTS

WO    WO 0000808        1/2000
WO    WO 2009/066293    5/2009
(Continued)

OTHER PUBLICATIONS

Yin, J. et al. Molecularly Mediated Thin Film Assembly of Nanoparticles on Flexible Devices: Electrical Conductivity versus Device Strains in Different Gas/Vapor Environment, ACS Nano, Aug. 2, 2011, 5(8), pp. 6516-6526.

(Continued)

*Primary Examiner* — Christopher Adam Hixson
*Assistant Examiner* — Michelle Adams
(74) *Attorney, Agent, or Firm* — Pearl Cohen Zedek Latzer Baratz LLP

(57) ABSTRACT

The present invention is directed to a sensor having continuous and discontinuous regions of conductive metallic nanoparticles capped with an organic coating which enables the detection of volatile organic compounds and/or water vapor. Continuous regions may exhibit a positive response upon exposure to volatile organic compounds and to water vapor, while discontinuous regions exhibit a positive response upon exposure to volatile organic compounds and a negative response upon exposure to water vapor.

8 Claims, 12 Drawing Sheets

Related U.S. Application Data

(60) Provisional application No. 61/582,547, filed on Jan. 3, 2012.

(51) Int. Cl.
  *G01N 27/12* (2006.01)
  *G01N 27/22* (2006.01)
  *G01N 33/00* (2006.01)

(58) Field of Classification Search
  CPC ......... G01N 33/497; G01N 2033/4975; B82Y 15/00; B82Y 30/00; A61B 5/082
  See application file for complete search history.

(56) References Cited

U.S. PATENT DOCUMENTS

| | | | |
|---|---|---|---|
| 9,625,341 | B2 | 4/2017 | Haick |
| 9,784,631 | B2 | 10/2017 | Haick |
| 10,663,420 | B2 * | 5/2020 | Haick .................. G01N 27/121 |
| 2005/0241935 | A1 | 11/2005 | Lewis |
| 2009/0049890 | A1 | 2/2009 | Zhong |
| 2009/0148690 | A1 | 6/2009 | Krasteva |
| 2010/0191474 | A1 | 7/2010 | Haick |
| 2012/0156099 | A1 | 6/2012 | Zhong |
| 2012/0245434 | A1 | 9/2012 | Haick |
| 2012/0245854 | A1 | 9/2012 | Haick |

FOREIGN PATENT DOCUMENTS

| | | |
|---|---|---|
| WO | WO 2009/118739 | 10/2009 |
| WO | WO 2010/079490 | 7/2010 |
| WO | WO 2011/148371 | 12/2011 |
| WO | WO 2012/023138 | 2/2012 |

OTHER PUBLICATIONS

Anderson, James Hunter Jr. and Parks, George A. (1968) Electrical conductivity of silica gel in the presence of adsorbed water. J Phys Chem 72(10):3662-3668.
Barash, Oma et al., (2009) Sniffing the Unique "Odor Print" of Non-Small-Cell Lung Cancer with Gold Nanoparticles. Small 5(22):2618-2624.
Barash, Oma et al., (2012) Classification of lung cancer histology by gold nanoparticle sensors. Nanomedicine 8 (5):580-589.
Brust, Mathias et al., (1994) Synthesis of Thiol-derivatised Gold Nanoparticles in a Two-phase Liquid-Liquid System. J Chem Soc Chem Commun 7:801-802.
Brust, Mathias and Kiely, Christopher J. (2002) Some recent advances in nanostructure preparation from gold and silver particles: a short topical review. Colloid Surf A 202(2-3)175-186.
Chow, Edith et al., (2009) Detection of organics in aqueous solution using gold nanoparticles modified with mixed monolayers of 1-hexanethiol and 4 mercaptophenol. Sens Actuat B 143(2):704-711.
Cooper, James Scott et al., (2010) Gold nanoparticle chemiresistor sensor array that differentiates between hydrocarbon fuels dissolved in artificial seawater. Anal Chem 82(9):3788-3795.
Daniel, Marie-Christine and Astruc, Didier (2004) Gold nanoparticles: assembly, supramolecular chemistry, quantum-size-related properties, and applications toward biology, catalysis, and nanotechnology. Chem Rev 104 (1):293-346.
Dasog, Mita and Scoti, Robert W. (2007) Understanding the oxidative stability of gold monolayer-protected clusters in the presence of halide ions under ambient conditions. Langmuir 23(6):3381-3387.
Dovgolevsky, Ekaterina et al., (2009) Chemically Sensitive Resistors Based on Monolayer-Capped Cubic Nanoparticles: Towards Configurable Nanoporous Sensors. Small 5(10):1158-1161.
Dovgolevsky, Ekaterina et al., (2010) Monolayer-Capped Cubic Platinum Nnoparticles for Sensing Nonpolar Analyst in Highly Humid Atmospheres. J Phys Chem C 114(33):14042-14049.
Fischetti, Massimo V. (1984) The importance of the anode field in controlling the generation rate of the donor states at the Si-Si02 interface. J Appl Phys 56(2):575-577.
Garg, Niti et al., (2010) Robust gold nanoparticles stabilized by trithiol for application in chemiresistive sensors. Nanotechnology 21(40):405501 (6 pages).
Guo, Jianli et al., (2007) Effect of trace residual ionic impurities on the response of chemiresistor sensors with dithiol-linked monolayer-protected gold (nano)clusters as sensing interfaces. Sens Actuat B 120(2):521-528.
Ha, Dong Han et al., (2002) Humidity effects on the conductance of the assembly of DNA molecules. Chem Phys Lett 355(5-6):405-409.
Haick, Hossam (2007) Chemical Sensors Based Molecularly Modified Metallic Nanoparticles. J Phys D 40:7173-7186.
Hakim, M. et al., (2011) Diagnosis of head-and-neck cancer from exhaled breath. Br J Cancer 104(10):1649-1655.
Han, Li et al., (2001) Core-shell nanostructured nanoparticle films as chemically sensitive interfaces. Anal Chem 73 (18):4441-4449.
Herrmann, J. et al., (2007) Tuning the Coulomb charging energy in cross-linked nanoparticle films. Phys Rev B 76:212201 (4 pages).
Hostetler, Michael J. et al., (1998) Alkanethiolate Gold Cluster Molecules with Core Diameters from 1.5 to 5.2 nm: Core and Monolayer Properties as a Function of Core Size. Langmuir 14(1):17-30 Herrmann, J. et al., (2007) Tuning the Coulomb charging energy in cross-linked nanoparticle films. Phys Rev B 76:212201 (4 pages).
Joseph, Yvonne et al., (2003) Self-Assembled Gold Nanoparticle/Alkanedithiol Films: Preparation, Electron Microscopy, XPS-Analysis, Charge Transport, and Vapor-Sensing Properties. J Phys Chem B 107(30):7406-7413.
Joseph, Yvonne et al., (2004) Chemiresistor coatings from Pt- and Au- nanoparticle/nonanedithiol films: sensitivity to gases and solvent vapors_ Sens Actuat B 98(2-3):188-195.
Joseph, Yvonne et al., (2007) Vapor Sensitivity of Networked Gold Nanoparticle Chemiresistors: Importance of Flexibility and Resistivity of the Interlinkage. J Phys Chem C 111(34):12855-12859.
Joseph, Yvonne et al., (2008) Gold Nanoparticle/Organic Networks as Chemiresistor Coatings: The Effect of Film Morphology on Vapor Sensitivity_ J Phys Chem C 112(32):12507-12514.
Kane, Jennifer et al., (2011) Chemistry, physics, and engineering of electrically percolating arrays of nanoparticles: a mini review_ JMaterChem21:16846-16858.
Konvalina, Gady and Haick, Hossam (2012) Effect of Humidity on NanoParticle-Based Chemiresistors: A Comparison between Synthetic and Real-World Samples_ ACS Appl Mater Interf 4(1):317-325.
Lee, Kyumin et al., (2007) Uniformly dispersed deposition of colloidal nanoparticles and nanowires by boiling. Appl Phys Lett91:173112.
Linko, Veikko et al., (2011) Defined-size DNA triple crossover construct for molecular electronics: modification, positioning and conductance properties. Nanotechnology 22(27):275610 (7 pages).
Marom, Ophir et al., (2012) Gold Nanoparticle Sensors for Detecting Chronic Kidney Disease and Disease Progression. Nanomedicine (Land) 7(5):639-650.
Mokari, Taleb {2011} Synthesis and characterization of hybrid nanostructures Nano Rev 2:5983 (9 pages).
Murphy, Catherine J. et al., {2005) Anisotropic Metal Nanoparticles: Synthesis, Assembly, and Optical Applications. J Phys Chem B 109(29):13857-13870.
Nath, N. and Chilkoti, A. (2002) A colorimetric gold nanoparticle biosensor: effect of particle size on sensitivity. In: Engineering in Medicine and Biology, 2002. 24th Annual Conference and the Annual Fall Meeting of the Biomedical Engineering Society EMBS/BMES Conference, 2002. Proceedings of the Second Joint vol. 1 pp. 574-575.
Paska, Yair et al., (2011) Enhanced Sensing of Nonpolar Volatile Organic Compounds by Silicon Nanowire Field Effect Transistors. ACS Nano 5(7):5620-5626.
Paska, Yair et al., (2012) Molecular Gating of Silicon Nanowire Field-Effect Transistors with Nonpolar Analytes. ACS Nano 6(1):335-345. Epub Dec. 23, 2011.

(56) References Cited

OTHER PUBLICATIONS

Pavanello, Michele et al., {2010} Modeling Hole Transport in Wet and Dry DNA. J Phys Chem B 114(13):4416-4423.

Peng, G. et al., (2009) Diagnosing lung cancer in exhaled breath using gold nanoparticles. Nat Nanotechnol 4 (10):669-673.

Peng, G. et al., (2010) Detection of lung, breast, colorectal, and prostate cancers from exhaled breath using a single array of nanosensors. Br J Cancer 103(4):542-551.

Raguse, Burkhard et al., (2009) Gold Nanoparticle Chemiresistor Sensors in Aqueous Solution: Comparison of Hydrophobic and Hydrophilic Nanoparticle Films. J Phys Chem C 113(34):15390-15397.

Rowe, Michael P. et al., (2004) Single-Phase Synthesis of Functionalized Gold Nanoparticles. Chem Mater 16 (18):3513-3517.

Ryan, J. T. et al., (2011) On the "Li-shaped" continuum of band edge states at the Si/SiO2 interface. Applied Physical Letters 99:223518 (3 pages).

Segev-Bar-Meital et al., (2012) Effect of Perforation on the Sensing Properties of Monolayer-Capped Metallic Nanoparticle Films. J Phys Chem C 116(29):15361-15368.

Shuster, Gregory et al., {2011) Classification of Breast Cancer Precursors through Exhaled Breath, Breast Cancer Research and Treatment. Breast Cancer Res Treat 126(3):791-796.

Steinecker, William H. et al., (2007) Model of Vapor-Induced Resistivity Changes in Gold-Thiolate Monolayer-Protected Nanoparticle Sensor Films. Anal Chem 79(13):4977-4986.

Terrill, Roger H. et al., (1995) Monolayers in Three Dimensions: NMR, SAXS, Thermal, and Electron Hopping Studies of Alkanethiol Stabilized Gold Clusters. J Am Chem Soc 177(4):12537-12548.

Tisch, Ulrike and Haick, Hossam (2010) Nanomaterials for Cross-Reactive Sensor Arrays. Bull MRS 35(1):797-803.

Tisch, Ulrike and Haick, Hossam (2010) Arrays of Chemisensitive Monolayer-Capped Metallic Nanoparticles for Diagnostic Breath Testing. Rev Chem Eng 26(5-6):171-179.

Wang, Guannan Roger et al., (2007) Correlation between nanostructural parameters and conductivity properties for molecularly-mediated thin film assemblies of gold nanoparticle. J Mater Chem 17(5):457-462.

Wang, Lingyan et al., (2010) Thin Film Assemblies of Molecularly-Linked Metal Nanoparticles and Multifunctional Properties. Langmuir 26(2):618-632.

Wuelfing, W. Peter et al., {2000) Electronic Conductivity of Solid-State, Mixed-Valent, Monolayer-Protected Au Clusters. J Am Chem Soc 122(46):11465-11472.

Wuelfing, W. Peter and Murray, Royce W. (2002) Electron Hopping through Films of Arenethiolate Monolayer-Protected Gold Clusters. J Phys Chem B 106(12):3139-3145.

Arregui et al., (2002) Simultaneous measurement of humidity and temperature by combining a reflective intensity-based optical fiber sensor and a fiber bragg grating_ IEEE Sensors J 2(5): 482-487.

Cook et al., (2009) Ambient intelligence: Technologies, applications, and opportunities. Pervasive and Mobile Computing 5:277-298.

Cosseddu et al., (2012) Strain Sensitivity and Transport Properties in Organic Field-Effect Transistors. IEEE Elec Dev Lett 33(1): 113-115.

Power et al., (2010) Silver nanoparticle polymer composite based humidity sensor. Analyst 135: 1645-1652.

Yao et al., (2010) A capacitive humidity sensor based on gold-PVA core-shell nanocomposites. Sensors and Actuators B: Chemical 145(1):327-333.

Yeh, Y. C. and Tseng, T. Y. (1989) Analysis of the d.c. and a.c. properties of K2O-doped porous Ba0.5Sr0.5TiO3 ceramic humidity sensor. J Mater Sci 24(8):2739-2745.

Zabet-Khosousi, Amir and Dhirani, Al-Amin (2008) Charge Transport in Nanoparticle Assemblies. Chem Rev 108(10):4072-4142.

Zhang, Fengxiang and Srinivasan, M.P. (2008) Layer-by-layer assembled gold nanoparticle films on amine-terminated substrates. J Coll Interf Sci 319(2):450-456.

Zilberman, Yael et al.,({2010) Carbon nanotube/hexa-peri-hexabenzocoronene bilayers for discrimination between nonpolar volatile organic compounds of cancer and humid atmospheres. Adv Mater 22(38):4317-4320.

Zilberman, Yael et al., (2011) Nanoarray of polycyclic aromatic hydrocarbons and carbon nanotubes for accurate and predictive detection in real-world environmental humidity. ACS Nano 5(8):6743-6753.

American Thoracic Society (ATS) and the European Respiratory Society (ERS)., ATS/ERS recommendations for standardized procedures for the online and offline measurement of exhaled lower respiratory nitric oxide and nasal nitric oxide, 2005. Am J Respir Grit Care Med 171(8):912-930.

* cited by examiner

MORPHOLOGY ENGINEERING OF CONDUCTIVE METALLIC NANOPARTICLES CAPPED WITH AN ORGANIC COATING

CROSS-REFERENCE TO RELATED APPLICATIONS

This patent application is a divisional of U.S. patent application Ser. No. 13/733,615 filed Jan. 3, 2013, now U.S. Pat. No. 10,663,420, and claims the benefit of U.S. Provisional Patent Application No. 61/582,547 filed on Jan. 3, 2012, which are incorporated by reference in their entirety.

FIELD OF THE INVENTION

The present invention is directed to the detection of volatile organic compounds and water vapor using a sensor comprising continuous and discontinuous regions of conductive metallic nanoparticles capped with an organic coating, wherein the continuous and discontinuous regions differentially detect volatile organic compounds and water vapor.

BACKGROUND OF THE INVENTION

Monolayer-capped metallic nanoparticles (MCNPs) have attracted significant attention during the past two decades, due to their unique bulk and surface properties (Mokari, Nano Rev. 2011, 2, 5983; Tisch & Haick, MRS Bull. 2010, 35(1), 797; Tisch & Haick, Rev. Chem. Eng. 2010, 26, 171; Haick, J. Phys. D 2007, 40, 7173; Daniel & Astruc. Chem. Rev. 2004, 104, 293). Sensors based on MCNP films are of special interest, mainly due to their controllable selectivity, high sensitivity, low detection limits, fast response and recovery times, small size, low-output impedance and easy integration in standard microelectronic devices (Joseph et al., J. Phys. Chem. C 2008, 112, 12507; Joseph et al., Sens. Actuat. B 2004, 98, 188; Herrmann et al., Phys. Rev. B 2007, 76, 212201; Wang et al., Langmuir 2010, 26, 618; Dovgolevsky et al., Small 2009, 5, 1158). These features allowed the successful implementation of MCNPs in a wide variety of applications, varying from detection of organic compounds in aqueous solutions (Raguse et al., J. Phys. Chem. C. 2009, 113, 15390; Chow et al., Sens. Actual. B 2009, 143, 704; Cooper et al., J. Anal. Chem. 2010, 82, 3788) to detection of trace analytes in the gas phase (Joseph et at, Sens. Actuat. B 2004, 98, 188; Joseph et al., J. Phys. Chem. B 2003, 107, 7406; Dovgolevsky et al., J. Phys. Chem. C 2010, 114, 14042), and even diagnosis of diseases from breath samples (Tisch & Haick, Rev. Chem. Eng. 2010, 26, 171; Peng et al., Nature Nanotechnol. 2009, 4, 669; Peng et al., Br. J. Cancer 2010, 103, 542; Barash et at, Small 2009, 5, 2618; Hakim et al., Br. J. Cancer 2011, 104, 1649; Marom et al., Nanomed. (Future Medicine) 2012, 7, 639; Shuster et al., Breast. Cancer Res. Treat. 2011, 126, 791) or in vitro samples (Barash et al., Small 2009, 5, 2618; Barash et al., Nanomed, Nanotech. Bio. Med. 2012, 8, 580). For use in chemiresistors, the metal cores, consisting either of a single metal or of an alloy of two or more metals, provide the electronic conductivity. The non-conductive organic matrix that coats the nanoparticles provides adsorption sites for the analyte molecules. The combination of metal cores and capping organic matrix provides two counteracting effects upon analyte adsorption: (i) three-dimensional swelling of the MNCP film that increases the interparticle tunneling distance for charge carriers and, hence, the film's resistance; and (ii) increasing the permittivity of the organic matrix around the metal cores that decreases the potential barriers between the metal cores, and, hence, the film's resistance (Haick, J. Phys. D 2007, 40, 7173). To tune the sensing signals of the MCNPs, a popular approach has been applied, namely to use derivatives of different backbones (Wang et al., J. Mater. Chem. 2007, 17, 457; Rowe et al., Chem. Mater. 2004, 16, 3513) and/or different electron-withdrawing or electron-accepting functional groups (Cooper et al., J. Anal. Chem. 2010, 82, 3788; Joseph et al., J. Phys. Chem. C. 2007, 111, 12855). This approach, however, incorporates synthesis challenges either of the molecular ligands or the MCNPs per se. In addition, different ligands usually result in different steric hindrance between the adjacent ligands adsorbed on the NP surface, different molecular densities on the NP surface, and therefore, different NP sizes and/or NP size distribution (Wang et al., J. Mater, Chem. 2007, 17, 457; Rowe et al., Chem. Mater. 2004, 16, 3513; Murphy et al., J. Phys. Chem. B 2005, 109, 13857). These changes affect the signal features, the chemical selectivity, the morphology, the baseline resistance, and/or the stability and performance over time of the MCNP chemiresistive films (Wang, et al., J. Mater. Chem. 2007, 17, 457; Garg et al., Nanotechnology 2010, 21, 405501; Wang et al., Langmuir 2010, 26, 618; Nath & Chilkoti, in Engineering in Medicine and Biology, 2002. $24^{th}$ Annual Conference and the Annual Fall Meeting of the Biomedical Engineering Society EMBS/BMES Conference, 2002, Proceedings of the Second Joint, Vol. 1, 2002, pp. 574-575; Rowe et al., Chem. Mater. 2004, 16, 3513; Joseph et al., J. Phys. Chem. C. 2007, 111, 12855; Cooper et al., J. Anal. Chem. 2010, 82, 3788; Joseph et al., J. Phys. Chem. B 2003, 107, 7406). As an illustrative example, Han et. al. (Anal. Chem. 2001, 73, 4441) have shown that a change in the NP size from 5 nm to 2 nm could affect the sensitivity of a specific MCNP chemistry, under similar exposure conditions to analytes, by ca. 35%. Dasog et al. (Langmuir 2007, 23, 3381) have shown that changes in the core size affect the oxidation rate of the organic ligands adsorbed on the NP surface, causing different drift in the sensing signal. Joseph et al. (J. Phys. Chem. C 21108, 112, 12507) showed that, for individual MCNP-dominated morphology, the MCNP film is not conductive and the chemiresistor device shows no response. For island-dominated morphology, charge transport becomes possible after a ID percolation pathway is formed. This percolation pathway contains large island-to-island gaps, which are the bottlenecks for charge transport due to their high resistance. Changes in permittivity (Haick, J. Phys. D 2007, 40, 7173; Joseph et al., J. Phys. Chem. B 2003, 107, 7406; Steinecker et al., Anal. Chem. 2007, 79, 4977) and swelling-induced reduction in the island-to-island gaps decrease the resistance of MCNP films. For continuous 3D morphology, where many percolation pathways exist, the MCNP film swells along the direction perpendicular to the surface after dosage with analytes. As a result, the interparticle distances along these percolation pathways increase, and accordingly, the resistance of the MCNP film increases. Likewise, a decrease (shrinking) in the interparticle separation within the continuous 3D morphology usually leads to a decrease in resistance. The effect of the dielectric constant of the analyte on the sensing signal is presumably weaker, thus reducing the magnitude of the positive response for some of the analytes. This explanation is based on the assumption that the sensing mechanism remains the same (swelling/shrinking and dielectric permittivity changes) when percolation pathways have already been formed. Despite advances in this field, many of the underlying molecular mechanisms generating the sensing signal remain only vaguely understood (Haick, J. Phys. D 2007, 40, 7173; Kane et al., J. Mater. Chem. 2011, 21, 16846; Zabet-Khosousi & Dhirani, Chem. Rev. 2008, 108, 4072; Shuster et al., J. Phys. Chem. Lett. 2011, 2, 1912).

WO 2009/066293, WO 2009/118739, WO 2010/079490, WO 2011/148371, WO 2012/023138, US 2012/0245434, and US 2012/0245854 to some of the inventors of the present invention disclose apparatuses based on nanoparticle conductive cores capped with an organic coating for detecting volatile and non-volatile compounds, particularly for cancer diagnosis.

A problem often encountered in the diagnosis of diseases through the analysis of volatile organic compounds (VOCs) in breath samples is the sensitivity of sensing apparatuses to humidity. Since breath samples may contain up to 80% relative humidity (RH), the VOCs are often masked by water vapor which consequently impedes sensor performance.

Han et al. (Chem. Phys. Lett. 2002, 355, 405) studied the effects of relative humidity on the conductance of the assembly of poly(dG)-poly(dC) and poly(dA)-poly(dT) DNA molecules. The results show that the conductance of a specimen consisting of multiple DNA molecules might be strongly affected by the relative humidity. A similar effect was reported for silica gel surfaces (Anderson & Parks, J. Phys. Chem. 1968, 72, 3662). Guo et al., (Guo et al., Sens. Actuat. B 2007, 120, 521) showed that when alkanethiol-capped AuNP films that contained traces of the phase-transfer reagent tetraoctylammonium bromide (TOABr) were used as chemiresistive sensors, the film resistance decreased when the sensors were exposed to water vapor.

In order to overcome the effect of water vapor on sensor performance, a sensing apparatus is typically equipped with a humidity sensor (Yeh & Tseng, J. Mat. Sci. 1989, 24, 2739) that independently measures the content of water vapor to be subtracted from the sensing signal thus affording the extraction of VOCs' signal.

There remains an unmet need of a sensing apparatus for detecting mixtures of VOCs in breath samples without dehumidifying the sample prior to measurement. There further remains a need for a humidity sensor having fast and reversible response upon exposure to water vapor.

SUMMARY OF THE INVENTION

The present invention provides a method of controlling the sensitivity of monolayer-capped metallic nanoparticle (MCNP) chemiresistive sensors towards volatile organic compounds (VOCs) and/or water vapor by varying the morphology of MCNP films to comprise continuous and discontinuous regions thereby enabling the differential detection of water vapor and VOCs. The present invention further provides concurrent detection of volatile organic compounds (VOCs) and water vapor using a single sensor and a process of manufacturing said sensor.

The present invention is based in part on the unexpected finding that a sensor comprising a continuous film of MCNP provides positive responses upon exposure to VOCs and to water vapor while a sensor comprising a film of MCNP which has discontinuous regions provides positive responses upon exposure to VOCs, but negative responses upon exposure to water vapor. The negative responses were at least 1 order of magnitude larger than the positive responses. Thus, by engineering the morphology of MCNP films mainly by systematic control of the percentage of film coverage of a substrate, concurrent detection of VOCs and water vapor can be achieved. These results provide a new avenue to tailor the sensing properties of the MCNP chemiresistors, thus widening the spectrum of potential applications of these sensors from VOCs' breath analysis to humidity detection.

According to a first aspect, the present invention provides a sensor for detecting an analyte selected from a volatile organic compound, water vapor, and combinations thereof, the sensor comprising continuous and discontinuous regions of conductive metallic nanoparticles capped with an organic coating, wherein the continuous and discontinuous regions differentially detect water vapor and volatile organic compounds.

According to one embodiment, the sensor provides the concurrent detection of volatile organic compounds (VOCs) and water vapor.

According to another embodiment, the present invention provides a sensor array comprising a plurality of sensors, each sensor comprising continuous and discontinuous regions of conductive metallic nanoparticles capped with an organic coating, wherein the continuous and discontinuous regions differentially detect water vapor and VOCs. In some embodiments, the sensor array comprises between 2 and 20 sensors, for example 4, 6, 8, 10, 12, 14, 16, 18 or 20 sensors. Each possibility represents a separate embodiment of the present invention.

In other embodiments, the sensor comprises a film of conductive metallic nanoparticles capped with an organic coating, the film comprising continuous and discontinuous regions. In further embodiments, the film comprising continuous and discontinuous regions of conductive metallic nanoparticles capped with an organic coating is formed on a substrate. In additional embodiments, the film comprising continuous and discontinuous regions of conductive metallic nanoparticles capped with an organic coating is characterized by a thickness ranging from about 1 nm to about 500 nm.

In some embodiments, the sensor is configured in a form selected from the group consisting of a capacitive sensor, a resistive sensor, a chemiresistive sensor, an impedance sensor, and a field effect transistor sensor. Each possibility represents a separate embodiment of the present invention.

In additional embodiments, the sensor is a chemiresistor comprising a film comprising continuous and discontinuous regions of conductive metallic nanoparticles capped with an organic coating formed on a substrate.

In particular embodiments, the substrate is a rigid substrate or a flexible substrate. Each possibility represents a separate embodiment of the present invention. In some embodiments, the substrate is selected from the group consisting of metals, insulators, semiconductors, semimetals, polymers, and combinations thereof. Each possibility represents a separate embodiment of the present invention. In other embodiments, the substrate is a polymer selected from the group consisting of polyimide, polyamide, polyimine, polyester, polydimethylsiloxane, polyvinyl chloride, and polystyrene. Each possibility represents a separate embodiment of the present invention. In one embodiment, the substrate comprises silicon dioxide. In another embodiment, the substrate comprises indium tin oxide.

In further embodiments, the continuous regions exhibit a positive response upon exposure to VOCs and to water vapor, and the discontinuous regions exhibit a positive response upon exposure to VOCs and a negative response upon exposure to water vapor.

In other embodiments, the discontinuous regions comprise voids ranging in size from about to about 10 nm to about 500 nm.

In various embodiments, the discontinuous regions comprise between about 3% and about 90% of voids.

In certain embodiments, the conductive metallic nanoparticles are selected from the group consisting of Au, Ag, Ni, Co, Pt, Pd, Cu, and Al nanoparticles and combinations thereof. Each possibility represents a separate embodiment of the present invention. In an exemplary embodiment, the conductive metallic nanoparticles are gold (Au) nanoparticles.

In other embodiments, the conductive metallic nanoparticles have a geometry selected from the group consisting of a cubic, a spherical, and a spheroidal geometry. Each possibility represents a separate embodiment of the present invention.

In various embodiments, the organic coating forms a monolayer on top of the conductive metallic nanoparticles. In specific embodiments, the organic coating comprises compounds selected from the group consisting of alkylthiols, arylthiols, alkylarylthiols, alkylthiolates, w-functionalized alkanethiolates, arenethiolates, (γ-mercaptopropyl)trimethyloxysilane, dialkyl disulfides and combinations and derivatives thereof. Each possibility represents a separate embodiment of the present invention. In further embodiments, the organic coating is 2-nitro-4-trifluoro-methylbenzenethiol. In other embodiments, the organic coating is 3-ethoxythiophenol.

In additional embodiments, the present invention provides a method for detecting an analyte selected from a volatile organic compound, water vapor and combinations thereof in the breath of a subject or in a sample, the method comprising the steps of: (i) providing a sensor comprising continuous and discontinuous regions of conductive metallic nanoparticles capped with an organic coating, wherein the continuous and discontinuous regions differentially detect water vapor and VOCs; (ii) exposing the sensor to the breath of a subject or to a sample comprising said analyte; and (iii) detecting a signal generated by said analyte using a detection means.

In further embodiments, the method of the present invention provides the detection of volatile organic compounds (VOCs), while concurrently determining the amount of water vapor, the method further comprising the steps of: (iv) determining the amount of water vapor from the detected signal; and (v) subtracting the amount of water vapor from the detected signal thereby allowing the detection of VOCs in the breath of a subject or in said sample. In accordance with these embodiments, the step of detecting a signal generated by said analyte using a detection means comprises the detection of a signal generated by VOCs and water vapor using different applied voltages.

According to a second aspect, the present invention provides a system for detecting an analyte selected from a volatile organic compound, water vapor, and combinations thereof, the system comprising: (i) a sensor array comprising a plurality of sensors, each sensor comprising continuous and discontinuous regions of conductive metallic nanoparticles capped with an organic coating, wherein the continuous and discontinuous regions differentially detect water vapor and VOCs; and (ii) a pattern recognition analyzer, wherein the pattern recognition analyzer receives sensor output signals and compares them to stored data.

In certain embodiments, the pattern recognition analyzer comprises at least one pattern recognition algorithm. Suitable pattern recognition algorithms include, but are not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the present invention.

In some embodiments, the method for detecting volatile organic compounds (VOCs), while concurrently determining the amount of water vapor comprises the use of a system comprising a plurality of sensors, each sensor comprising continuous and discontinuous regions of conductive metallic nanoparticles capped with an organic coating, and a pattern recognition analyzer, the method further comprises the step of analyzing the detected signal using a pattern recognition analyzer which receives sensor output signals and compares them to stored data.

In various embodiments, the detection means comprises a device for measuring changes in resistance, conductance, alternating current (AC), frequency, capacitance, impedance, inductance, mobility, electrical potential, optical property or voltage threshold. Each possibility represents a separate embodiment of the present invention.

In some embodiments, the VOCs to be detected are selected from polar organic molecules, non-polar organic molecules and combinations thereof. Each possibility represents a separate embodiment of the present invention.

According to yet another aspect, the present invention provides a method of manufacturing a sensor for detecting an analyte selected from a volatile organic compound, water vapor and combinations thereof, the method comprising the step of forming a film comprising continuous and discontinuous regions of conductive metallic nanoparticles capped with an organic coating on a substrate, wherein the discontinuous regions comprise voids which are produced in the presence of water vapor during film formation process. In accordance with these embodiments, the water vapor present during film formation process is used to control the sizes and percentages of the voids in said discontinuous regions.

In certain embodiments, the amount of water vapor present in the film formation process ranges from about 1%, to about 20%, relative humidity. In particular embodiments, the amount of water vapor present during film formation process ranges from about 5'% to about 10% relative humidity.

In further embodiments, the sensor, sensor array and system of the present invention can be used for breath analysis, wherein the analyte to be detected is a VOC or mixtures thereof.

In exemplary embodiments, the present invention provides the diagnosis of various diseases in a subject, preferably a human, through the detection of VOCs indicative of said diseases. Encompassed within the scope of the present invention is the diagnosis of cancer through the detection of breath VOCs which are indicative of cancer. In some embodiments, the present invention provides the diagnosis of cancer selected from the group consisting of lung, brain, ovarian, colon, prostate, kidney, bladder, breast, oral, and skin cancers. Each possibility represents a separate embodiment of the invention.

In additional embodiments, the sensor and sensor array of the present invention can be used as a means to detect relative humidity. In one embodiment, the present invention provides a breath sensor, wherein said breath sensor detects the presence of proximate breath through the detection of its relative humidity. In accordance with these embodiments, the breath sensor can be used for monitoring breath thus affording the detection and treatment of sleep apnea and other respiratory diseases, and the prevention of sudden infant death syndrome (SIDS). The present invention thus provides a method of monitoring the breathing of a subject comprising detecting a signal generated by water vapor present in each breath of a subject. The sensor/sensor array of the present invention may be in a form of a nose clip or a stick-patch, optionally connected to a device which produces a human perceptible signal (e.g. an audible alarm) when breath is not being detected.

In further embodiments, the present invention provides a method of activating an input device by a subject comprising detecting a signal generated by water vapor present in the breath of said subject, and changing the configuration of a switch by the detected signal thereby activating said input device. In some embodiments, the sensor of the present invention operates as a humidity sensor which activates an input device by an on/off switch (e.g. humidity-triggered switch). In accordance with these embodiments, the detection of a signal generated by water vapor present in exhaled breath of a subject is being used to change the configuration of a switch thus enabling the activation of an input device. In certain embodiments, the sensor of the present invention can be used to turn on a switch by the detection of water vapor from breath directly exhaled by the subject, wherein the subject is selected from the group consisting of a quadriplegic patient, a paraplegic patient, an amputee, a patient with a spinal cord injury, a physically impaired person, and any combination thereof. Each possibility represents a separate embodiment of the present invention. In further embodiments, the input device comprises at least one of a "Sip and Puff" switch, a pager button, an emergency button, an on/off button for universal remote devices (e.g. TV, AC, Video, Stereo, and the like), a light switch, a door opening switch optionally combined with a video-intercom, an elevator button, a smartphone controller, and a selection (click) button for an IR guided cursor. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIGS. 1A, 1B) 16% RH (S1); (FIGS. 1C, 1D) 31% RH (S2); and (FIGS. 1E, 1F) 54% RH (S3).

FIGS. 3A-3B. AFM images of: (FIG. 3A) S1 and (FIG. 3B) S3 films.

(FIG. 4A) S1 sensors, (FIG. 4B) S2 sensors, and (FIG. 4C) S3 sensors, produced in three different casting cycles (cycle A, black; cycle B, red; and cycle C, blue), upon exposure to different levels of RH.

FIGS. 5A-5D. Normalized responses, $\Delta R/R_{end}$, of S1 (black), S2 (red) and S3 (blue) to various concentrations of: (FIG. 5A) 2-ethylhexanol; (FIG. 5B) decane; and (FIG. 5C) Water vapor, (FIG. 5D) $\Delta R/R_{end}$ of S3 upon exposure to various RHs. $R_{end}$ is the resistance at the end of the sensing signal and $\Delta R$ is the $R_{end}$-corrected resistance change upon exposure of the sensor to the analyte.

FIGS. 6A-6B. Normalized responses, $\Delta R/R_{base}$ of: (FIG. 6A) NTMBT-AuNP sensors (S4, black; S5, red; and S6, green); and (FIG. 6B) ETP-AuNP sensors (S7, black; S8, red; and S9, blue) on flexible substrate vs humidity in a constant temperature. $R_{base}$ is the baseline resistance.

(FIG. 7A) ETP-AuNP sensor having baseline resistance of 18 MΩ (S7); (FIG. 7B) ETP-AuNP sensor having baseline resistance of 29 MΩ (S8); and (FIG. 7C) ETP-AuNP sensor having baseline resistance of 31 MSΩ (S9).

(FIG. 8D) Magnification of the −0.005\1 to +0.005V region of the S3 sensor, presented in FIG. 8C.

(FIG. 9B) with applied voltage (5 V). (FIG. 9C) Magnification of the central area of FIG. 9B.

DETAILED DESCRIPTION OF THE INVENTION

Figure 1A:
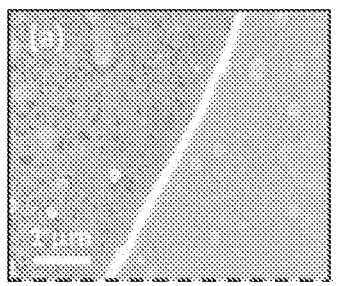
FIGS. 1A-1F. FE-HRSEM images taken from three sensors produced by drop casting NTMBT-AuNP solution on the electrode structure at three different relative humidity (RH) conditions as follows.
Figure 1C:
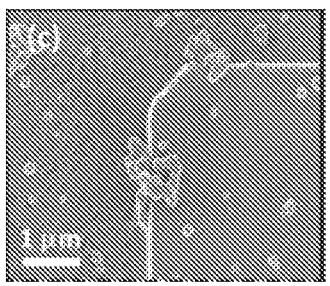
Figure 1E:
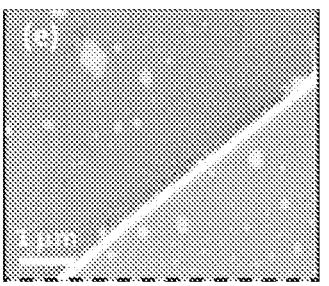

The present invention provides a method for determining the presence of an analyte selected from a VOC, water vapor and combinations thereof in a sample. The present invention thus provides a sensor which comprises conductive metallic nanoparticles capped with an organic coating that are arranged in continuous and discontinuous regions which allow the differential detection of VOCs and water vapor.

Water molecules are a main confounding environmental factor that screens the sensing signals obtained from the VOCs in breath analysis applications. Unexpectedly it is now disclosed that by engineering the morphology properties of MCNP films via controlling their coverage on the device surface, double information can be extracted from the breath sample, by measuring both the amount of water vapor and the presence of breath biomarker VOCs using the same sensor. The present inventors have discovered unexpectedly, that continuous MCNP film morphology exhibits positive responses upon exposure to VOCs and to water vapor, consistent with the swelling and dielectric sensing mechanisms. In contrast, discontinuous films exhibit positive responses upon exposure to VOCs, but a high-magnitude negative response upon exposure to water vapor. These findings are attributed to ionic conduction from the MCNP free domains (voids on the surface) to the MCNP domains, where conduction through tunneling also exists.

Nanoparticle (NP) based chemiresistors typically exhibit two types of responses: a reduction or enhancement of resistivity. While small response values, up to 10-15%, could be explained by the swelling and the dielectric phenomenon when conduction is by tunneling between adjustment NPs, some sensors exhibit a very large relative response of up to −90% and more, which cannot be explained by this model. As demonstrated herein, the negative responses result from specific-morphology of NPs based sensors and are correlated with the presence and size of a hysteresis loop in the I-V scan. This large negative response (as well as the hysteresis loop) is shown to be the result of ionic conduction through condensate water over the substrate. This happens when the NPs film is perforated, namely it comprises voids. Water vapor condensate on these voids, and the applied voltage ionizes the water and/or the silicone dioxide (the substrate), allowing current to flow. This conduction does not involve the VOCs. Hence this effect is only proportional to the amount of condensed water. The ionization is dependent on the applied voltage. Thus, at different voltages there are more or less conductive ionic species (for a given amount of water condensate on the surface). By probing at different voltages, it is possible to extract the contribution of ionic conduction from the overall conduction by tunneling and ionic flows together. As demonstrated herein, higher humidity levels provide higher conduction of ionic species using the same applied voltage. Since the ionic conduction is proportional to the humidity level (the amount of condensed water on the surface), it is possible to calculate the relative humidity of the surrounding from the ionic current. Preliminary calibration by exposures to known amounts of water vapor or known relative humidity levels and measuring the thus obtained responses can also be performed.

The present invention overcomes the drawbacks of the background art by providing the use of a single sensor for detecting volatile organic compounds and water vapor. US 2010/0191474 and Dovgolevsky et al. (J. Phys. Chem. C, 2010, 114(33), 14042) to one of the inventors of the present invention disclose sensors which exhibit low sensitivity to polar analyte vapor, especially water vapor. It was not previously realized that a film of nanoparticles which comprises continuous and discontinuous regions can be utilized as a sensor which is sensitive to both non-polar and polar VOCs including water vapor, thereby enabling the concurrent detection of VOCs and water vapor in a sample. For breath analysis applications, the reduction of water from the signal of VOCs of interest is crucial since water is not a marker of interest, but is present in breath samples in large amount (as high as 80% relative humidity). The present invention provides a novel method to achieve this goal by controlling the morphology of MCNP, without the need for complicated synthesis approaches of the organic ligands and/or MCNPs. The effect of morphology variations within a continuous MCNP film, where percolation pathways already exist, on the sensing of volatile organic compounds (VOCs) and water molecules enables to widen the spectrum of potential applications of MCNP chemiresistors.

Currently available humidity sensors include capacitive humidity sensors, resistive humidity sensors, dew point and thermal conductivity. For most applications, the environmental conditions dictate the choice of sensor technology. Resistive, capacitive, and thermal conductivity sensing technologies each offer distinct features. Resistive sensors are interchangeable, usable for remote locations, and cost effective. Capacitive sensors provide wide RH range and condensation tolerance, and, if laser trimmed, are also interchangeable. Thermal conductivity sensors perform well in corrosive environments and high temperatures. All of these sensors provide response times which range from several seconds to tens of seconds, with the time required to return to baseline being even longer. Most dew point based sensors are large and relatively expensive. The average response time of most sensors remains above 1 second. Thus, these sensors are often not sensitive to rapid changes in humidity on the scale of single seconds.

The sensor of the present invention provides rapid responses to small changes in humidity with a response time of less than 1 second. The present invention thus offers a humidity sensor having relatively small dimensions and which produces fast response and return (recovery) times with low production costs and power consumption. The present invention provides a sensor for the detection of a VOC or water vapor or the concurrent detection of both for use as a breath analyzer, a breath sensor or a breath switch having very fast response and return times (<1 second) and high sensitivity to VOCs as well as water vapor (<1% changes in RH are detectable).

Disclosed herein is a sensor comprising metallic nanoparticles capped with an organic coating, wherein the metallic nanoparticles capped with an organic coating are arranged in continuous and discontinuous regions thus allowing the differential detection of VOCs and water vapor. According to the principles of the present invention, continuous MCNP film morphology exhibits positive responses upon exposure to VOCs and to water vapor while discontinuous MCNP film morphology exhibits positive responses upon exposure to VOCs and negative responses upon exposure to water vapor. Without being bound by any theory or mechanism of action, continuous MCNP film morphology provides the detection of analytes through the swelling and dielectric sensing mechanisms, while discontinuous MCNP film morphology provides the detection of analytes through ionic conduction from the substrate in MCNP-free domains (voids) to the MCNP domains, side-by-side with tunneling conduction within MCNP domains.

Accordingly, the present invention provides a simple strategy for controlling the sensing properties of a sensor comprising conductive metallic nanoparticles capped with an organic coating, by engineering their morphology through varying the percentage of coverage of the substrate. The morphology of the conductive metallic nanoparticles capped with an organic coating comprises continuous and discontinuous regions comprising voids to allow the detection of water, VOCs, or a combination thereof. In some embodiments, the present invention provides the simultaneous detection of water and VOCs, present in the same sample (e.g. a breath sample).

Within the scope of the present invention are conductive metallic nanoparticles including, but not limited to, Au, Ag, Ni, Co, Pt, Pd, Cu, and Al nanoparticles and combinations thereof. Each possibility represents a separate embodiment of the present invention.

The conductive metallic nanoparticles are coated with an organic coating. In exemplary embodiments, the organic coating comprises a monolayer of organic molecules. Suitable coating of the conductive metallic nanoparticles includes, but is not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkanethiolates, arenethiolates, (γ-mercaptopropyl)tri-methyloxysilane, dialkyl disulfides and combinations thereof. Each possibility represents a separate embodiment of the present invention. Exemplary organic coating includes, but is not limited to, 2-nitro-4-trifluoro-methylbenzenethiol and 3-ethoxythiophenol. Each possibility represents a separate embodiment of the present invention.

Sensors comprising conductive metallic nanoparticles capped with an organic coating can be synthesized as is known in the art, for example using the two-phase method (Brust et al., J. Chem. Soc Chem. Commun., 1994, 7, 801) with some modifications (Hostetler et al., Langmuir 1998, 14, 17). In a non-limiting example, $AuCl_4^-$ is transferred from aqueous $HAuCl_4 \cdot xH_2O$ solution to a toluene solution by the phase-transfer reagent TOAB. After isolating the organic phase, excess thiols are added to the solution. The mole ratio of thiol:$HAuCl_4 \cdot xH_2O$ can vary between 1:1 and 10:1, depending on the thiol used. This is performed in order to prepare mono-disperse solution of gold nanoparticles in an average size of about 3-6 nm. Exemplary procedures include, but are not limited to, thiol: Au mole ratios of 10:1 and 1:1 for dodecanethiol and butanethiol-capped gold nanoparticles, respectively at an average size of about 5 nm. After vigorous stirring of the solution, aqueous solution of the reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with e.g. 2-mercaptobenzimidazole can be synthesized by the ligand-exchange method from pre-prepared hexanethiol-capped gold nanoparticles. In a typical reaction, excess of thiol, 2-mercaptobenzimidazole, is added to a solution of hexanethiol-capped gold nanoparticles in toluene. The solution is kept under constant stirring for a few days in order to allow as much ligand conversion as possible. The nanoparticles are purified from free thiol ligands by repeated extractions. The conductive metallic nanoparticles may have any desirable geometry including, but not limited to, a cubic, a spherical, and a spheroidal geometry. Each possibility represents a separate embodiment of the present invention.

In some embodiments, the synthesized conductive metallic nanoparticles capped with an organic coating are assembled (e.g. by a self-assembly process) to produce a film having continuous and discontinuous regions. The term "film", as used herein, corresponds to a two dimensional configuration of conductive metallic nanoparticles capped with an organic coating. The film is typically deposited on top of a substrate. Suitable substrates within the scope of the present invention include substances which may be rigid or flexible. Within the scope of the preset invention are flexible substrates which may also be stretchable. Exemplary substrates include, but are not limited to, metals, insulators, semiconductors, semimetals, polymers, and combinations thereof. Each possibility represents a separate embodiment of the present invention. In some embodiments, the substrate is a polymer which may be polyimide (e.g. Kapton), polyamide, polyimine (e.g. polyethylenimine), polyester (e.g. polyethylene terephthalate, polyethylene naphthalate), polydimethylsiloxane, polyvinyl chloride, polystyrene and the like. Each possibility represents a separate embodiment of the present invention. In one embodiment, the substrate comprises silicon dioxide (for example glass or a silicon wafer coated with $SiO_2$). In another embodiment, the substrate comprises indium tin oxide.

According to the principles of the present invention, the conductive metallic nanoparticles capped with an organic coating are arranged in continuous and discontinuous regions on the substrate. The discontinuous regions comprise voids which range in sizes from about 10 nm to about 500 nm. The density of voids typically ranges between about 3% and about 90% of the area of the discontinuous region.

The present invention discloses for the first time that a correlation exists between the morphology of the film of conductive metallic nanoparticles capped with an organic coating and the relative humidity (RH) conditions at time of deposition. Hence, the present invention provides a manner of controlling the sizes and percentages of voids as a function of relative humidity present during the formation process. This allows direction of the sensors' characteristics towards the desired applications and needs. When needed, the possibility of ionic conduction due to water can be completely eliminated from the sensor, and when needed, it could be achieved, by alternation of the relative humidity conditions present during the process of formation. Accordingly, it is possible to detect an analyte of interest, wherein the analyte can be a polar or a non-polar VOC or water vapor or both.

Films or assemblies of conductive metallic nanoparticles capped with an organic coating can be formed on surfaces using a variety of techniques well known in the art. Exemplary techniques include, but are not limited to, i. Random deposition from solution by drop casting, spin coating, spray coating and other similar techniques.
  ii. Field-enhanced or molecular-interaction-induced deposition from solution.
  iii. Langmuir-Blodgett or Langmuir-Schaefer techniques.
  iv. Soft lithographic techniques, such as micro-contact printing (mCP), replica molding, micro-molding in capillaries (MIMIC), and micro-transfer molding (mTM).
  v. Various combinations of Langmuir-Blodgett or Langmuir-Schaefer methods with soft lithographic techniques.
  vi. Printing on solid-state or flexible substrates using an inject printer designated for printed electronics.

The sensors of the present invention can be configured as any one of the various types of electronic devices, including, but not limited to, capacitive sensors, resistive sensors, chemiresistive sensors, impedance sensors, field effect transistor sensors, and the like, or combinations thereof. Each possibility represents a separate embodiment of the present invention. In a non-limiting example, the sensors of the present invention are configured as chemiresistive sensors (i.e. chemiresistors).

The present invention further encompasses a system comprising a sensor array comprising a plurality of sensors (for example between 2 and 20 sensors), each sensor comprising conductive metallic nanoparticles capped with an organic coating having a morphology which comprises continuous and discontinuous regions. The system further comprises a pattern recognition analyzer.

According to the principles of the present invention, the pattern recognition analyzer receives sensor output signals and analyzes them by at least one pattern recognition algorithm to produce an output signature. By comparing an unknown signature with a database of stored or known signatures, volatile organic compounds and, in particular volatile breath biomarkers can be identified. The analyzer utilizes pattern recognition algorithms comprising artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the present invention.

Additional algorithms suitable for identifying patterns of volatile organic compounds and optionally quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms Each possibility represents a separate embodiment of the present invention. In some embodiments, the Fisher linear discriminant analysis (FLDA) and canonical discriminant analysis (CDA) and combinations thereof are used to compare the output signature and the available data from the database. Other classification techniques may also be employed. After analysis is completed, the resulting information can be displayed on a display or transmitted to a host computer.

In certain embodiments, the sensors of the present invention comprise one or more conducting elements. The conducting elements may include a source and a drain electrode separated from one another by a source-drain gap. The sensors may further comprise a gate electrode wherein the sensor signal may be indicative of a certain property of the capped nanoparticles under the influence of a gate voltage. In some embodiments, the sensor signal may be indicative of a capacitance property of the capped nanoparticles. Within the scope of the present invention are sensors comprising continuous and discontinuous regions of conductive metallic nanoparticles capped with an organic coating formed on a substrate comprising a plurality of electrodes (e.g. Au electrodes). In various embodiments, the distance between adjacent electrodes which defines the sensing area ranges between about 0.5 µm to about 3 mm.

The sensor signal may be induced, according to the principles of the present invention by a change in any one or more of conductivity, resistance, impedance, capacitance, inductance, or optical properties of the sensors upon exposure to VOCs and/or water vapor. Changes in the optical properties of the sensor(s) can be measured using e.g., spectroscopic ellipsometry.

The sensor signal is detected by a detection means. Suitable detection means include devices which are susceptible to a change in any one or more of resistance, conductance, alternating current (AC), frequency, capacitance, impedance, inductance, mobility, electrical potential, optical property and voltage threshold. Each possibility represents a separate embodiment of the present invention. In additional embodiments, the detection means includes devices which are susceptible to swelling or aggregation of capped nanoparticles as well as devices which are susceptible to a change in any one or more of optical signal, florescence, chemiluminsence, photophorescence, bending, surface acoustic wave, piezoelectricity and the like. Each possibility represents a separate embodiment of the present invention.

In some embodiments, the sensor signal is obtained by swelling of the conductive metallic nanoparticles capped with an organic coating. In other embodiments, the sensor signal is obtained by ionic conduction from the substrate in regions free of conductive metallic nanoparticles capped with an organic coating and/or by tunneling conduction in regions comprising conductive metallic nanoparticles capped with an organic coating. In further embodiments, the ionic conduction is controlled by the magnitude of an applied voltage.

The present invention further provides a method for detecting VOCs in breath directly exhaled by a subject or in a sample while concurrently determining the amount of water vapor. The method comprises the exposure of a sensor comprising continuous and discontinuous regions of conductive metallic nanoparticles capped with an organic coating to breath or said sample and detecting a signal generated by VOCs and water vapor using a detection means. In particular embodiments, a plurality of signals can be detected, each signal being collected at different applied voltages. Accordingly, the amount of water vapor can be deduced from the detected signal(s) and consequently subtracted from said signal(s) thereby allowing the detection of VOCs in said sample. It is to be understood that the VOCs to be detected comprise non-polar organic molecules as well as polar organic molecules, and combinations of polar and non-polar organic molecules. Each possibility represents a separate embodiment of the present invention.

In specific embodiments, the sample comprising VOCs and water is a breath sample. The collection of a breath sample, according to the principles of the present invention, can be performed in any manner known to a person of ordinary skill in the art. In exemplary embodiments, the breath sample may be collected using a breath collector apparatus. Specifically, the breath collector apparatus is designed to collect alveolar breath samples. Exemplary breath collector apparatuses within the scope of the present invention include apparatuses approved by the American Thoracic Society/European Respiratory Society (ATS/ERS); Am. J. Respir. Crit. Care Med. 2005, 171, 912). Alveolar breath is usually collected from individuals using the off-line method.

The present invention further provides breath analysis which is directed to the diagnosis of various diseases or disorders. Encompassed by the present invention is the diagnosis of cancer by the detection of VOCs indicative of cancer while concurrently determining the amount of water vapor. In some embodiments, the cancer to be diagnosed includes, but is not limited to, lung, brain, ovarian, colon, prostate, kidney, bladder, breast, oral, and skin cancers. Each possibility represents a separate embodiment of the invention.

The present invention further provides the use of the sensor of the present invention as a breath sensor, a breath monitor and/or a breath switch. Each possibility represents a separate embodiment of the present invention. The present invention thus provides a method in situ monitoring of humidity levels in breath directly exhaled by the subject on the sensor, suitable for applications such as, but not limited to diagnosing and treating sleep apnea and other respiratory diseases by detection of water vapor using a sensor as described herein. The present invention further provides a method of preventing sudden infant death syndrome (SIDS) by detection of water vapor present in infant breath using a sensor as described herein and alerting through generating a human perceptible signal if infant breath is not detectable. The present invention further provides methods of using a sensor as described herein as an on/off breath switch by detection of water vapor present in breath (single or few subsequent breaths). Accordingly, the sensor detects a signal generated by water vapor present in the breath of a subject and activates an input device by changing the configuration of an on/off switch. The on/off breath switch, according to the principles of the present invention can be used in instances where touch-buttons are not-applicable, for example by quadriplegic patients, paraplegic patients, amputees, patients with a spinal cord injury, physically impaired persons, and the like. Each possibility represents a separate embodiment of the present invention. Suitable applications of the breath switch\button include, but are not limited to, replacement of "Sip and Puff" switch, a pager button, an emergency button, an on/off button for universal remote devices (e.g. TV, AC, Video, Stereo, etc.), a light switch, a door opening switch optionally combined with a video-intercom, an elevator button, a smartphone controller, and a selection (click) button for an IR guided cursor. Each possibility represents a separate embodiment of the present invention. The sensors of the present invention may be incorporated into a device, said device being in a form of a nose clip or a stick-patch, as is known in the art. The sensor of the present invention can easily be tailored by controlling the percentage of continuous and discontinuous regions thus enabling the tuning of the switch to trigger at different humidity levels.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" is generally employed in its sense including "and/or" unless the content clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Synthesis, Preparation and Characterization of MCNP Chemiresistors Gold (III) chloride trihydrate ($HAuCl_4 \cdot 3H_2O$), tetraoctylammonium bromide (TOAB), sodium borohydride, 2-nitro-4-trifluoro-methylbenzenethiol (NTMBT), and 3-ethoxythiophenol (ETP) were purchased from Sigma-Aldrich. All reagents were at analytical grade and were used as received. Spherical gold nanoparticles (AuNPs; 3-6 nm in diameter) were synthesized as described in Peng et al., Nature Nanotechnol. 2009, 4, 669; and Brust & Kiely, Colloid. Surf. A 2002, 202, 175. Briefly, a solution of $HAuCl_4$ was added to a stirred solution of TOAB in toluene. After 10 minutes stirring, the lower aqueous phase was removed. Organic ligands and sodium borohydride were subsequently added to the toluene phase. After 3 hours at ice temperature, the lower aqueous phase was removed and the toluene phase was subsequently evaporated by rotary evaporation. After first washing with cold ethanol, the solution was kept at 5° C. for 18 hours until complete immersion was achieved. The dark brown precipitate was filtered off and washed with ethanol. Chemiresistors were prepared by drop casting aliquots of the same MCNP solution under constant relative humidity (RH) atmosphere, in the range of 10-50% RH, on interdigitated electrodes containing 24 pairs of Au electrodes (5 μm width and 25 μm spacing between adjacent electrodes) on a silicon wafer with 1000 nm $SiO_2$ film. In each relative humidity casting condition, 12 chemiresistors were prepared and characterized. The microstructure and morphology of MCNP films were characterized by an optical microscope (Nikon Eclipse L150) and by field emission scanning electron microscopy (Carl Zeiss Ultra Plus FE-SEM), respectively.

The FE-HRSEM analysis was performed with the aid of two mam detectors: Secondary electrons (SE) detector and back scattered electrons (BSE) detector. The SE detector provides high-resolution imaging of fine surface morphology in which inelastic electron scattering caused by the interaction between the sample's electrons and the incident electrons results in the emission of low-energy electrons close to the surface of the sample. The topography of surface features influences the number of electrons that reach the secondary electron detector from any point on the scanned surface. This local variation in electron intensity creates the image contrast that reveals the surface morphology. The BSE detector provides image contrast as a function of elemental composition as well as surface topography in which backscattered electrons are produced by the elastic interactions between the sample and the incident electron beam. These high-energy electrons can escape from much deeper locations than secondary electrons, so surface topography is not as accurately resolved as in secondary electron imaging. The production efficacy for backscattered electrons is proportional to the sample material's mean atomic number, which results in an image contrast which depends on the composition. Accordingly, materials with high atomic numbers appear brighter than materials with low atomic numbers in a backscattered electron image.

The morphology of the MCNP films was additionally examined by a tapping mode Atomic Force Microscope (AFM) (Dimension 3100 with Nanoscope Ma controller, Veeco Instruments Inc.) that is equipped with a 100×100 μm$^2$ scanner. Silicon cantilevers with a normal resonance frequency of 160 kHz and spring constants of 5 N/m (NSC14/AlBs, MikroMasch, Estonia) were used. All images were captured with a scan rate of 1-2 Hz and with a pixel resolution of 512×512.

In addition, chemiresistors (S4-S9) were prepared by drop casting aliquots of 3-ethoxythiophenol (ETP-AuNP) and NTMBT-AUNP solutions on a flexible foil of polyvinyl chloride (PVC) under constant humidity and temperature conditions.

Exposure to Analytes

Thirty-six chemiresistors were mounted on a custom PTFE circuit board with 40 separated sensor sites (4 sites were left empty). The board was mounted inside a stainless steel test chamber with a volume of less than 300 cm$^3$. Controlled gas concentrations (20-80 ppm of decane or 2-ethylhexanol), were produced by a commercial dynamic liquid injection dilution (DLID) system (Umweittechnik MCZ, Germany). Purified dry air (4.1-7.0% RH; <0.3 ppm impurities content) from a commercial zero-air system (NGA 600-25 MD, Umweittechnik MCZ, Germany) was used as carrier gas. The DUD system mixes a constant purified air flow (100±1 cm$^3$/min) with a constant mass flow source of vaporized VOCs. The air/VOC mixture exiting the DLID system was then diluted with two flow controlled dilution air streams: (i) dry air obtained directly from the zero-air system, and (ii) humidified air generated by the system's humidifier module. The total VOC concentration at the system output was set by controlling the mass flow rate of the vaporized VOC(s) and the total volumetric air flow rate. The VOC(s) and RH output were monitored by a commercial photoionization detector (PID; ppbRAE 3000) and by a commercial RH sensor (±2% accuracy), respectively. The sensing experiments were performed by monitoring the response of the NICNIP and environmental sensors (i.e., RH, temperature and pressure sensors) to the VOCs generated by the DUD system, A Keithley datalogger device (model 2701 DMM) controlled by a custom LabVIEW program was used to sequentially acquire resistance readings from the sensor array and voltage readings from the environmental sensors. Constant currents in the range of $0.7$-$1.10^4$ µA were used for resistance measurements. A typical exposure cycle involved a 5 minutes vacuum step (<50 mTorr), followed by 5 minutes exposure to the test vapor under stagnant conditions, and ended with another 5 minutes vacuum step. Each acquisition cycle of the entire sensor array was completed in less than four seconds. Each exposure cycle for either water vapor or organic analytes was typically repeated three times to test for reproducibility.

PH Indicator

Bromothymol blue PH-Indicator was dissolved in ethanol and deionized water. The indicator was drop-cast on an interdigitated electrode and allowed to dry under a +5V or 0 V bias between the adjacent electrodes of the interdigitated device.

Example 1: Characterization of MCNP Films

Aliquots of nitro-4-trifluoro-methylbenzenethiol-capped gold nanoparticle (NTMBTAuNP) solution were drop-cast on interdigitated electrodes under various humidity atmospheres: 16% RH (S1), 31% RH (S2) and 54% RH (S3). Similar baseline resistance, electrical properties and responses to VOCs and water were obtained for ~90% of the sensors produced in each humidity condition. The varying Relative Humidity (RH) conditions led to the formation of high baseline resistances for representative sensors S1 and S2 (~18 MΩ) and to the formation of relatively low baseline resistance for S3 (~5 MΩ). FIGS. 1A-1F present field emission high resolution scanning electron microscopy (FE-HRSEM) images of the S1-S3 films. As seen in these figures, drop-casting under different RH conditions controlled the morphology of the NTMBT-AuNP films. The films deposited under a high humidity level (54% RH) resulted in more uniform layers with less aggregates. In contrast, films deposited under low humidity levels showed less uniform layers with more aggregates. Particularly, the formation of the S1 and S2 films was interrupted by pinholes that are free of NTMBT-AuNPs, thus causing the films to be discontinuous (perforated). The S1 and S2 films included aggregates of NTMBT-AuNPs, with larger aggregates for S1 (10 s-100 s µm) and medium aggregates for S2 (up to 50 µm). Unlike the S1-S2 films, the S3 film was characterized by a uniform and continuous NTMBT-AuNP layer that has neither pinholes nor aggregates. Similar morphological features could be obtained through advanced assembly or deposition techniques (Lee et al., J. Appl. Phys. 2007, 91, 173112; Zhang & Srinivasan, J. Coll. Interf. Sci. 2008, 319, 450).

Figure 2:
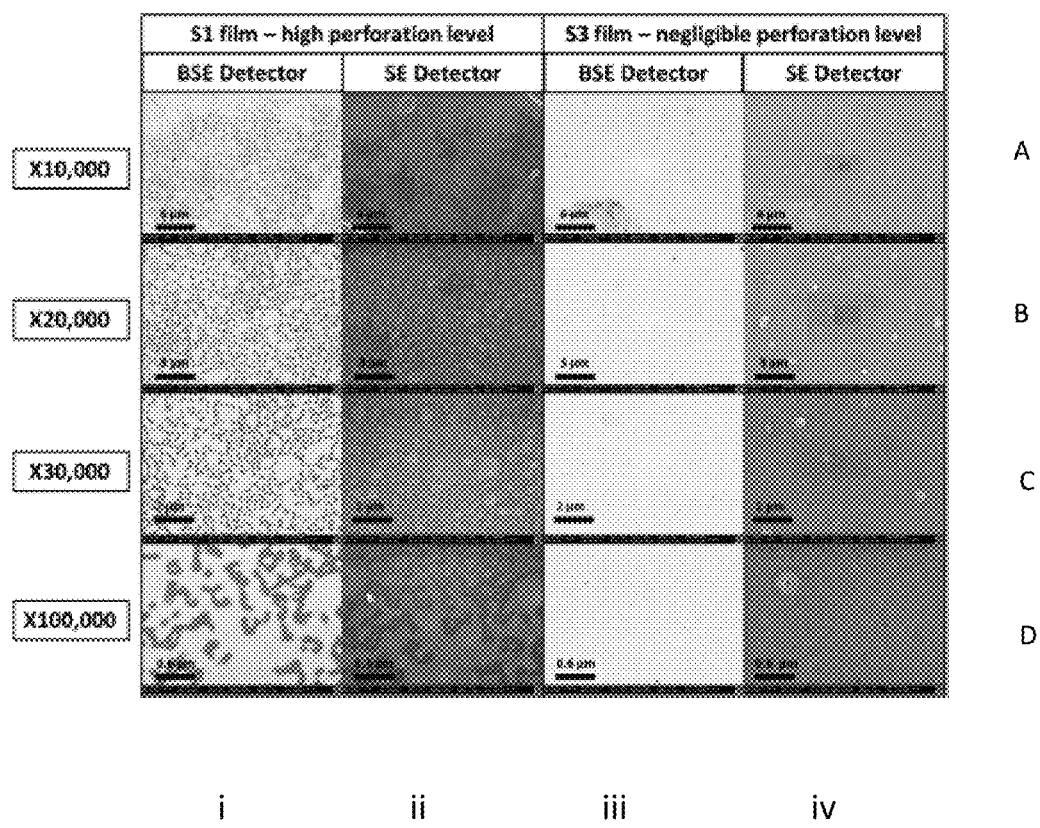
FIG. 2. HR-SEM images of representative S1 (columns i and ii) and S3 (columns iii and iv) films at different magnifications (panels A-D), using both BSE (columns i and iii) and SE (columns ii and iv) detectors.

To further study the morphology nature of the S1-S3 films, combined BSE and SE analyses were performed for two representative samples. The white areas which are produced using the BSE detector are attributed to the MCNP film, whereas the dark areas are attributed to the $SiO_2$ surface which has lower average atomic number as compared to the MCNPs. FIG. 2 shows that S3 has a flatter morphology as compared to S1. For S3, images that were obtained from the BSE detector showed only bright areas with almost no color variation. In other words, the BSE detector showed only MCNP film without any evidence of $SiO_2$ pinholes or areas. For S1, the BSE detector showed some degree of perforation, with the $SiO_2$ substrate seen as small dark pinholes. Thus, the S1 sensor showed a higher degree of $SiO_2$ area compared to the S3 sensor. The HR-SEM confirmed that S1 has a perforated MCNP film structure, with voids that reach the $SiO_2$ surface (the dark areas) while the S3 film is continuous with relatively rare defects of perforation, which do not seem to reach the underlying $SiO_2$ surface.

Figures 3A, 3B:
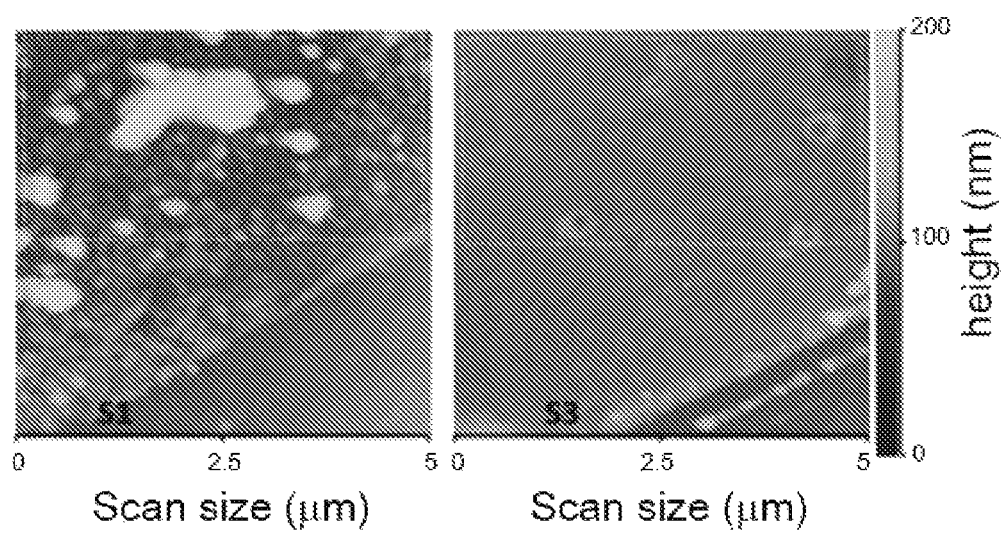

The same S1 and S3 films were scanned using AFM (FIGS. 3A-3B). The scanned areas were 5×5 µm with an intentionally imposed scratch to allow measurement of the MCNP film above the $SiO_2$ substrate. The measurement of surface roughness of the area enclosed with the broken line rectangle in FIGS. 3A-3B allowed calculation of the films' roughness as follows: (i) Surface area difference that represents the difference between the image's 3D surface area and its 2D footprint area was calculated as 8.83% for S1 and 1.03% for S3; and (ii) Rq, which is the root-mean-square average of height deviations taken from the mean data plane (rms) was calculated as 40.4 nm for S1 and 3.74 nm for S3. Thus, the AFM analysis revealed that the average thickness of both S1 and S3 films was similar (~15 nm), while the rms roughness of S1 (40.4 nm) was much higher than that of S3 (3.74 nm).

Example 2: Response to VOCs and Water Vapor

Figure 4A:
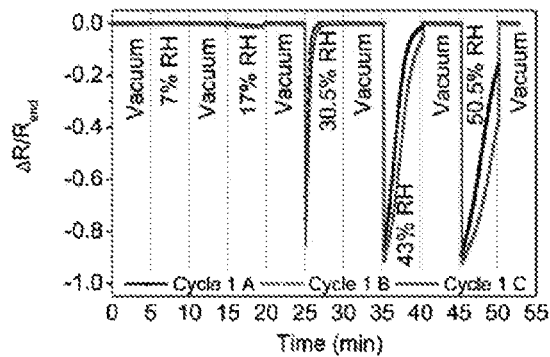
FIGS. 4A-4C. Normalized responses, $\Delta R/R_{end}$, of three randomly selected.
Figure 4B:
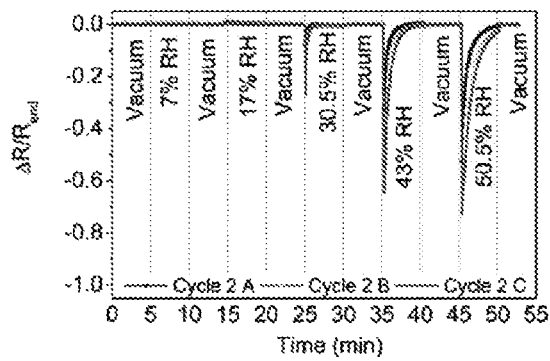
Figure 4C:
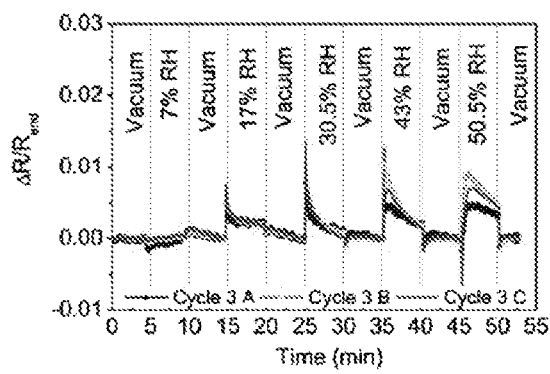
Figure 5A:
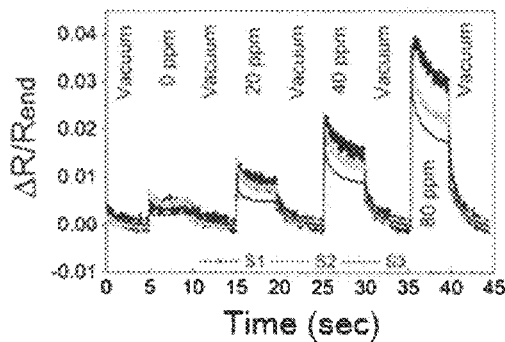
Figure 5B:
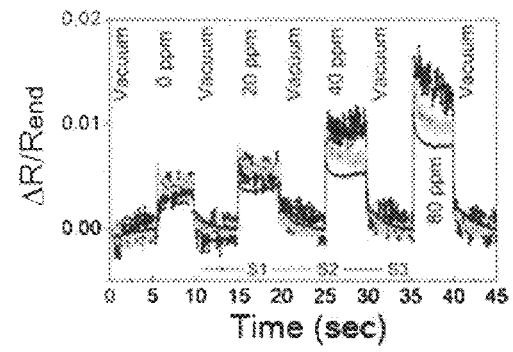
Figure 5C:
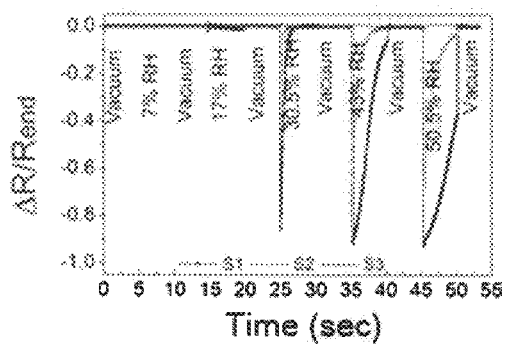
Figure 5D:
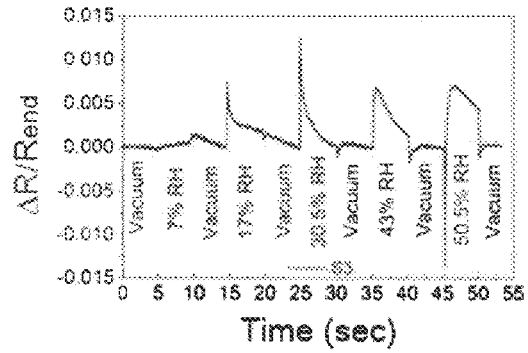
Figure 6A:
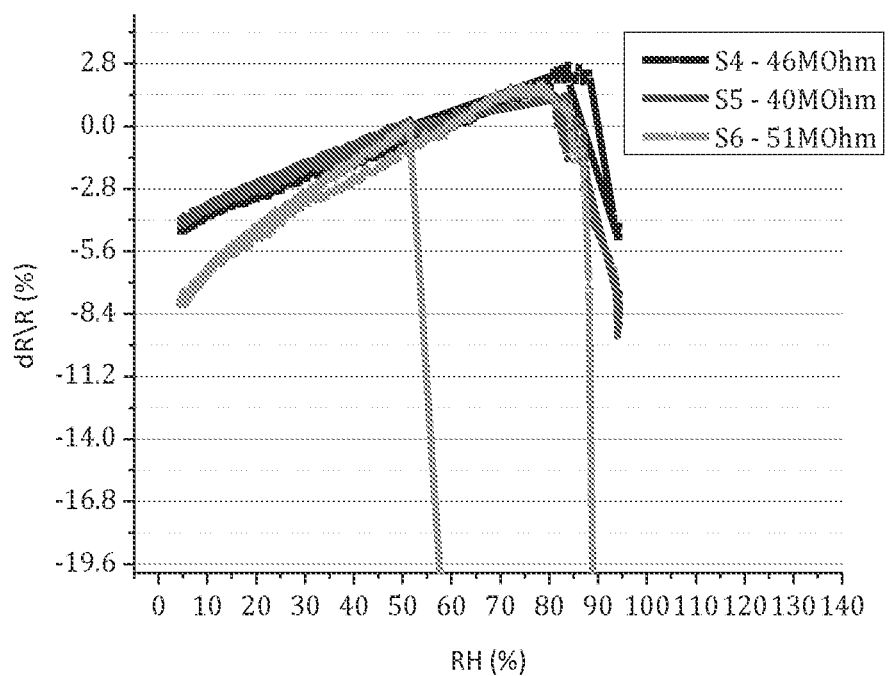
Figure 6B:
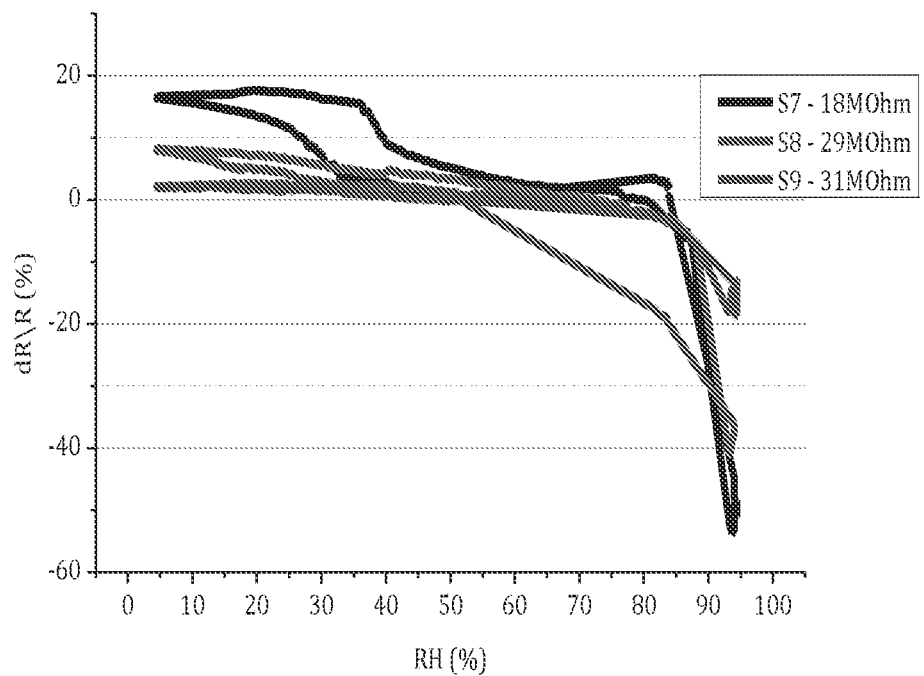

S1-S3 sensors were exposed to various concentrations of decane, 2-ethylhexanol (with constant background humidity level of ~5%) and water, FIGS. 4A-4C show the responses obtained from triplicates of S1, S2, and S3, prepared in different casting cycles, to different humidity levels. $R_{end}$ is the resistance at the end of the sensing signal and ΔR is the $R_{end}$-corrected resistance change upon exposure of the sensor to the analyte. The notation Cycle ij describes the sensor's type, via the numerical digit (i=1, 2 or 3), and the casting cycle, via the alphabetical capital letters (j=A, B, or C). Evidently, the results show that the variations obtained within a specific batch production (i.e., under a specific RH condition) are much smaller than variations in responses from different batch productions (i.e., production under different RH conditions). FIGS. 5A-5D show the resistance responses, $ΔR/R_{end}$, of the sensors upon exposure to analytes. It is noted that the term "positive response" refers to an increase in the resistance (ΔR>0) above the baseline resistance and that the term "negative response" refers to a decrease in the resistance (ΔR<0) below the baseline resistance. As seen in these figures, S3 yielded the best signal-to-noise ratio (SNR), compared to S1 and S2, upon exposure to VOCs. In contrast, S3 exhibited the lowest responses, compared to S1 and S2, upon exposure to humidity conditions. For example, the SNR obtained upon exposure to 20 ppm decane was 3.6 for S1, 5.6 for S2, and 19.7 for S3. The responses of S1-S3 upon exposure to decane and 2-ethylhexanol exhibited a reduction in conductivity and an enhancement in the NTMBT-AuNP resistance. The higher the amount of VOC or water concentration, the higher the responses of S3 (see FIGS. 5A-5D), indicating sensing by a swelling effect (Joseph et al., J. Phys. Chem. C 2008, 112, 12507; Joseph et al., J. Phys. Chem. B 2003, 107, 7406). S1 and S2 showed nonlinear correlation with the RH, with positive $\Delta R/R_{end}$ at low RH levels and negative $\Delta R/R_{and}$ at high RH levels (Table 1). The results also show that the kinetics of the NTMBT-AuNP sensing response are affected by the RH level. The negative response to water rapidly declined towards the baseline resistance from the moment of exposure. The decline was slower when higher concentrations of water were introduced. For example, 66 $R/R_{start}$= −65% ($\Delta R$ is the baseline-corrected resistance change at the beginning of the signal upon exposure of the sensor to the analyte and $R_{start}$ is resistance at the beginning of the sensing signal) was obtained immediately after exposure of S2 to 43% RH, but declined to $\Delta R/R_{end}$=−0.80% after 5 minutes. $\Delta R/R_{start}$=−73% was obtained immediately after exposure of S2 to 50.5% RH, but declined to $\Delta R/R_{end}$=−3.2% after 5 minutes, even though the water vapor was still present in the chamber in both instances. Without being bound by any theory or mechanism of action, the reduction of the resistance in response to water vapor is associated with the ionization of condensed water on the $SiO_2$ substrate and the conduction by the generated ions. The fast decline in the response (back to baseline resistance) is attributed to the accumulation of these ions at the vicinity of the oppositely charged electrodes. At the moment of exposure to a humid sample, water condenses on the silicone-oxide and under the applied voltage, ionization occurs. The amount of produced ions depends on the applied potential and the amount of water. The movement of the produced ions towards the electrodes spikes a relatively large electrical current that rapidly declines once the ions reach the electrodes. A similar behavior was observed using flexible substrates on a humidity cycle from 5% RH to 94% RH and vice versa (FIGS. 6A-6B).

Another potential source of such ionic currents is the conduction through defects and trap states generated in the $Si/SiO_2$ interface (Ryan et al., App. Phys. Lett. 2011, 99, 223516/1-3; Fischetti, J. Appl. Phys. 1984, 56, 575). To test this, S1-S3 films were prepared on circular interdigitated electrodes (24 pairs of Au electrodes, 5 μm width and 25 μm spacing between the adjacent electrodes) on glass substrates rather than on $Si/SiO_2$ substrates. The resulting devices exhibited strong reductions in resistance upon exposure to water and maintained positive responses upon exposure to VOCs, similar to the sensing properties of S1-S3 films on $Si/SiO_2$ substrates. Additionally, the glass-based S1-S3 sensors exhibited similar correlation between the $A_{hysteresis}$ and perforation level compared to the S1-S3 films on $Si/SiO_2$ substrates. Without being bound by any theory or mechanism of action, this observation suggests that the negative responses of S1 and S2 toward water are not due to conduction through defects and trap states generated in the $Si/SiO_2$ interface

TABLE 1

Calculated $\Delta R/R_{start}$ and $\Delta R/R_{end}$ for S1, S2 and S3 under different humidity levels

| S3 | | S2 | | S1 | | RH/Sensor |
|---|---|---|---|---|---|---|
| $\Delta R/R_{end}$ | $\Delta R/R_{start}$ | $\Delta R/R_{end}$ | $\Delta R/R_{start}$ | $\Delta R/R_{end}$ | $\Delta R/R_{start}$ | response (%) |
| 0.02 | 0 | 0.18 | 0.1 | 0.17 | 0.16 | 7 |
| 0.24 | 0.75 | −0.13 | 1 | −0.9 | −2.33 | 17 |
| 0.15 | 1.25 | −0.3 | −26.9 | 0.3 | −85.7 | 31 |
| 0.25 | 0.6 | −0.8 | −65 | −6.3 | −91.8 | 43 |
| 0.57 | 0.6 | −3.2 | −73 | −40.5 | −92.7 | 51 |

Example 3: Modeling and Sensing Relative Humidity Conditions

In order to study the response of sensors comprising discontinuous regions to water vapor, the normalized responses, $\Delta R/R_{base}$ of sensors of NTMBT-AuNP and ETP-AuNP vs humidity (FIGS. 3A-3B) were modeled to produce a linear equation which represents the change in resistance as a function of relative humidity (without including relative humidity levels which produce a drop in resistance due to the accumulation of ions at the vicinity of the oppositely charged electrodes). A blind test analysis of 20% of the samples was performed using S4 and S5 sensors. The accuracy of the blind test was determined as 86% for both sensors (Table 2). Thus, the sensors of the present invention provide a reliable measurement of the relative humidity of a sample by measuring the change in resistance from baseline resistance upon exposure to the sample. An increase in accuracy can further be achieved through post-processing analysis (e.g. increasing the number of line cycles, inducing a delay and oversampling).

Figure 7A:
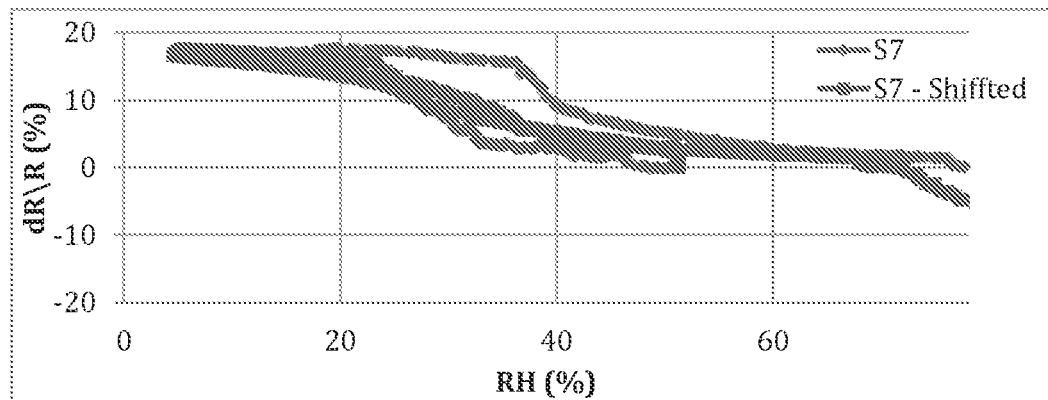
FIGS. 7A-7C Normalized responses, $\Delta R/R_{base}$ of: ETP-AuNP sensors versus humidity with 0.2 seconds response time (blue) and 1 minute response time (red).
Figure 7B:
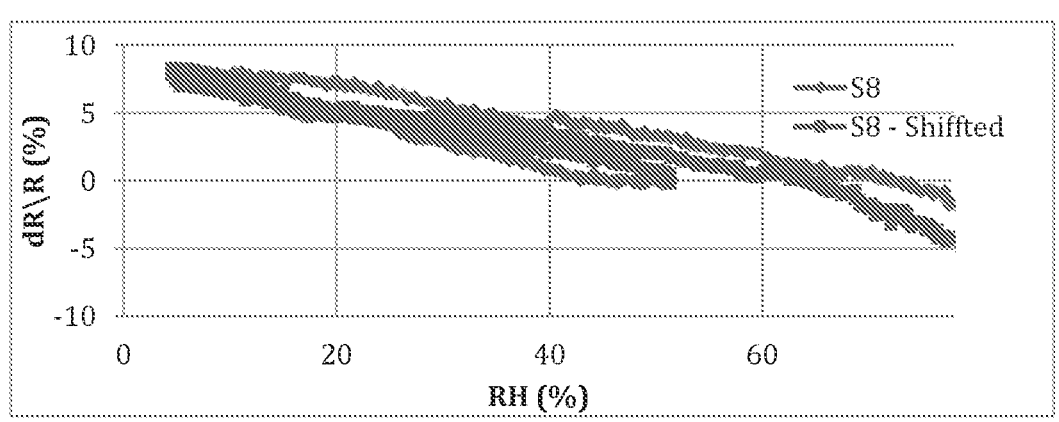
Figure 7C:
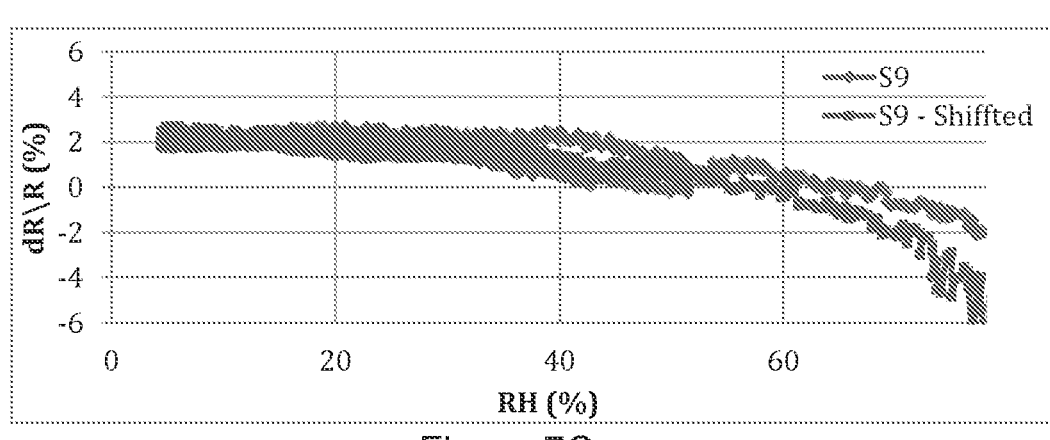
Figure 8A:
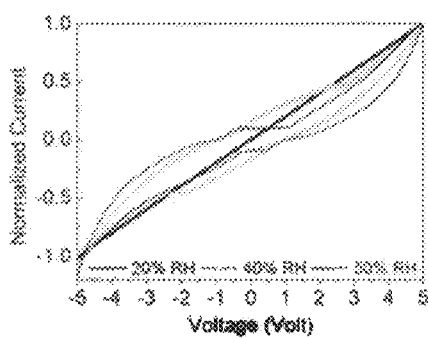
FIGS. 8A-8D. Normalized current-voltage (I-V) curves for (FIG. 8A) S1, (FIG. 8B) S2, and (FIG. 8C) S3 at ~20% RH (black), 40% RH (red) and 50% RH (blue).
Figure 8B:
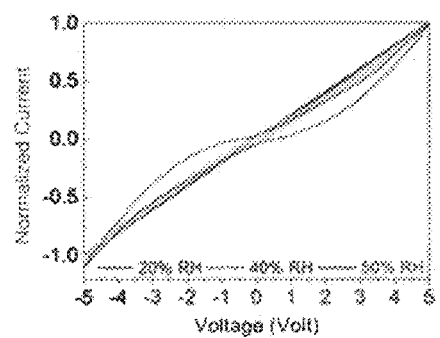
Figure 8C:
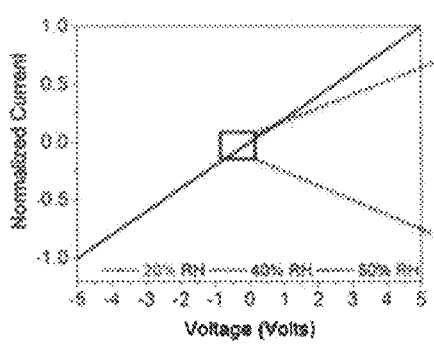
Figure 8D:
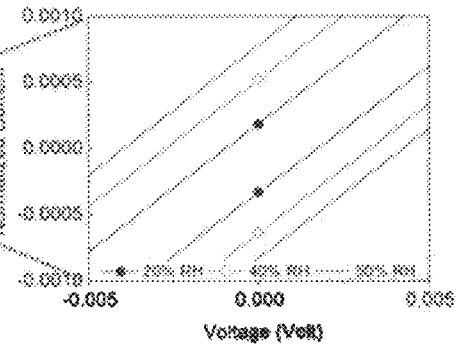
Figures 9A, 9B:
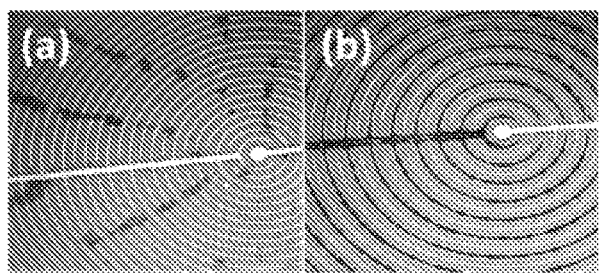
FIGS. 9A-9C. Bromothymol Blue indicator on an interdigitated electrode after drying (FIG. 9A) without applied voltage.
Figure 9C:
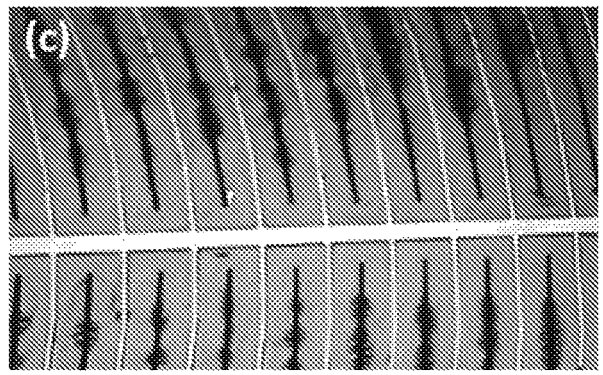

In order to determine the response time of the sensors (the time between two adjacent measurements of resistance), the hysteresis of the normalized responses vs. relative humidity was calculated for a shift of 0.2 seconds and 1 minute of the normalized responses. The response time of sensors of NTMBT-AuNP was determined as 0.2 seconds or lower and the response time of sensors of ETP-AuNP was determined as 1 minute (FIGS. 7A-7C). Thus, the sensors of the present invention provide fast response and return times to different levels of relative humidity.

TABLE 2

Statistical analysis of blind test for the modeling of NTMBT-AuNP versus relative humidity

| Sensor | $\Delta R/R/1\%$ RH | Accuracy | Average variance | Equation |
|---|---|---|---|---|
| S4 | +0.085 | 86% | ±1.2% RH | $\Delta R/R = 0.085\ RH - 4.768$ |
| S5 | +0.082 | 86% | ±1.1% RH | $\Delta R/R = 0.082\ RH - 4.402$ |

Example 4: Hysteresis in Current-Voltage Characteristics

FIGS. 8A-8D show normalized current-voltage (I-V) curves of S1-S3 upon exposure to various RH levels. I-V curves were recorded after reaching steady state conditions of relative humidity in the exposure chamber. I-V curve measurement can be compared to the initial response upon exposure to relative humidity $\Delta R/R_{start}$ since it was the first applied voltage on the sensors, thus making the first ionization only at the time of measurement. As seen in these figures, S1 showed a negligible hysteresis at 20% RH, but large hysteresis upon exposure to higher RH levels. The normalized hysteresis area, $A_{Hysteresis}$, was calculated by summing the results of subtractions of the maximum normalized current value from its minimum value for each given voltage. $A_{Hysteresis}$ was equal for both 40% and 50% RH ($A_{Hysteresis}$~2.2 a.u.), suggesting a possible saturation in the response mechanism (Table 3). S2 showed no hysteresis upon exposure to 20% RH, but a large hysteresis was present under 40% RH ($A_{Hysteresis}$ ~0.3 a.u.) and an even larger hysteresis under 50% RH ($A_{hysteresis}$ ~1.2 a.u.). For 40% and 50% RH, nonlinear I-V curves were observed for S1 and S2 and Ohmic curves were observed for S3. The $A_{hysteresis}$ of S3 was negligible under all RH levels applied in the current study (see FIGS. 8C, 8D). I-V curves were also measured during exposures to dry air containing either decane or 2-ethylhexanol. No hysteresis was obtained from any of the sensors during the exposure process to these VOCs. For S1 and S2, a correlation between $\Delta R/R_{start}$ and $A_{Hysteresis}$ was found upon exposure to water. $R_{start}$ is the resistance at the beginning of the sensing signal (average of the first 5 points of the exposure process) and $\Delta R$ is the baseline-corrected resistance change at the beginning of the signal upon exposure of the sensor to an analyte. For S2, the results showed $\Delta R/R_{start}$=1% at 17.5% RH and $A_{Hysteresis}$ [18] 0 (a.u.) at 20% RH; $\Delta R/R_{start}$=−65% at 43% RH and $A_{Hysteresis}$~0.3 (a.u.) at 40% RH; and $\Delta R/R_{start}$=−80.5% at 50.5% RH and $A_{Hysteresis}$ ~½ (a.u.) at 50% RH. S1 exhibited slightly negative ($\Delta R/R_{start}$=−2.3%) responses upon exposure to 17.5% RH and $A_{Hysteresis}$ ~0.02 (a.u.) upon exposure to 20% RH. In contrast, S1 exhibited highly negative responses upon exposure to 43% RH ($\Delta R/R_{start}$=−91.8%) and to 50.5% RH ($\Delta R/R_{start}$=−92.7%), with $A_{Hysteresis}$ ~2.2 (a.u) for both RH levels.

TABLE 3

Calculated $A_{Hysteresis}$ for S1, S2 and S3 under 20%, 40%, and 50% RH levels

| S3 | S2 | S1 | RH |
|---|---|---|---|
| 0.02 | 0.03 | 0.02 | 20% |
| 0.04 | 0.3 | 2.2 | 40% |
| 0.03 | 1.2 | 2.2 | 50% |

The positive responses of S1 and S2 towards VOCs comply with the swelling mechanism (see FIGS. 2A-2B). In contrast, the correlation between $\Delta R/R_{start}$ and $A_{Hysteresis}$ upon exposure to humidity rules out the involvement of a swelling mechanism in S1 and S2. Additionally, the rapid decline of the responses toward the baseline during exposure to water (see FIG. 2C), rules out sensing response via a tunneling mechanism (Pavanello et al., J. Phys. Chem. B 2010, 114, 4416; Linko et al., Nanotechnology 2011, 22, 275610) since the resistance does not reach a new steady-state value. Without being bound by any theory or mechanism of action, the negative response of S1 and S2 towards water vapors is related to the hysteresis effect (Linko et al., Nanotechnology 2011, 22, 275610). Accordingly, the sensing process in S1 and S2 might be obtained by the conduction of ionic species (Han Ha et al., Chem. Phys. Lett. 2002, 355, 405; Anderson & Parks, J. Phys. Chem. 1968, 72, 3662), rather than by tunneling (Wuelfing et al., J. Am. Chem. Soc. 2000, 122, 11465; Wuelfing & Murray, J. Phys. Chem. B 2002, 106, 3139; Terrill et al., J. Am. Chem. Soc. 1995, 117, 12537).

Example 5: Conductivity in Relative Humidity Conditions

In order to study the effect of RH on the conductivity of the sensors, a pH indicator was used. The conductivity is dominated by ionic current as follows: $\sigma = en\mu$, where e is the elementary charge, n is the ionic concentration, and $\mu$ is the ion mobility. Assuming the mobility is not affected by RH (in the range of 15-50% RH), the conductivity can be calculated as follows: $\sigma \propto n \propto \exp(-e^2/(2\varepsilon rRT))$, where E is the local dielectric constant, R is the gas constant and r is the equilibrium distance of the charges in neutral species (Anderson & Parks, J. Phys. Chem. 1968, 72, 3662; Yeh & Tseng, J. Mat. Sci. 1989, 24, 2739).

A Bromothymol Blue indicator (having a blue color in a basic environment and an orange-red color in an acidic environment) was dissolved in water and ethanol. The indicator was drop-cast on the same interdigitated electrodes used for the MCNP sensors, after which it was allowed to dry. This process was performed twice: with and without applying voltage between the two electrodes. Color changes at the various electrodes were compared after the droplet dried (FIGS. 6A-6C). As seen in FIG. 6A, when the indicator dries with no applied voltage, there were no significant color variations near or between the electrodes. When the indicator was dried under applied voltage (FIGS. 6B, 6C) pronounced color variations near the two electrodes were observed. In particular, a blue color was clearly seen near the electrode on which a positive bias was applied, indicating a basic environment. In a similar manner, the orange-red contour surrounding the negatively biased electrode indicated that acidic environment was created. Without being bound by any theory or mechanism of action, when applying voltage, the generated $OH^-$ species move towards the positive electrode, thus creating a high pH level which turns the indicator blue. The $H_3O^+$ species move towards the negative electrode, thus creating low pH conditions which turn the indicator orange-red in the vicinity of the electrode. Accordingly, these observations show that water is ionized under the applied voltage, and that these ions take part in the conduction process during the sensing process. When the RH is increased, there is an increase in the local dielectric constant, which enhances the dissociation of water and the ionization of the MCNP-free domains of the chemiresistive films, viz. the $SiO_2$ domains.

Figure 1B:
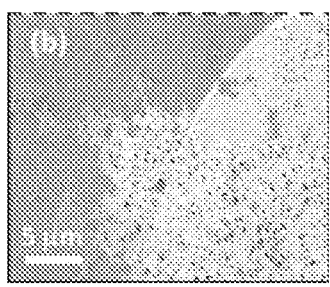
Figure 1D:
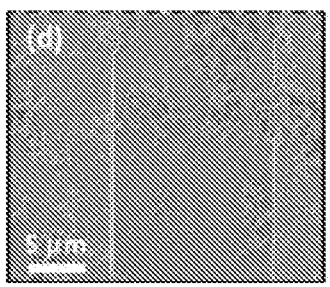
Figure 1F:
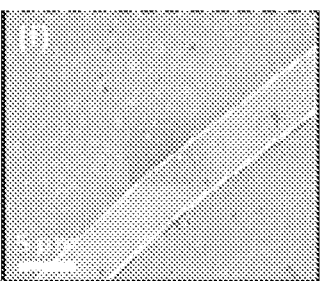
Figure 10:
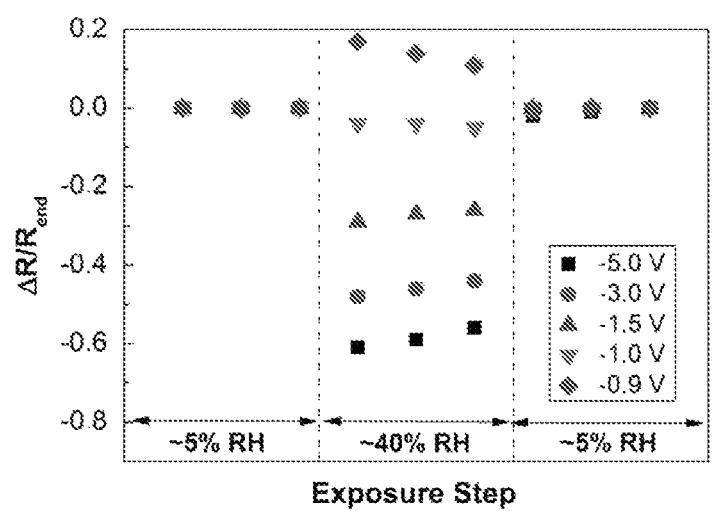
FIG. 10. Calculated relative response of S2 to 40% RH compared to 5% RH, under different voltages (−5.0 V, black; −3.0 V, red; −1.5 V, blue; −1.0 V, pink; and −0.9 V, green).

For film morphologies containing many pinholes, gaps and topographical features (MCNP-free domains; FIGS. 1A, 1B), the exposure to water vapors results in enhanced adsorption and local condensation of water on the MCNP-free domains, viz. on the $SiO_2$ surface, leading to ionic currents and to a temporal reduction in resistance upon exposure (FIG. 5C). A high degree of porosity (perforation) provides a larger area and more adsorption ($SiO_2$) sites for water. Without being bound by any theory or mechanism of action, the higher the amounts of adsorbed water ($\varepsilon$=78.5), the higher the local dielectric constant (Paska et al., ACS NANO 2011, 5, 5620) and the oxide dissociation to ions (Anderson & Parks, J. Phys. Chem. 1968, 72, 3662). Accordingly, films containing less voids/pinholes exhibit small $A_{Hysteresis}$ and a weak resistance reduction upon exposure to a specific RH level while high RH levels lead to a strong decline in the resistance and increase in the $A_{Hysteresis}$. Thus, by controlling the humidity level and the applied voltage, the ionic conduction of the MCNP sensors can be controlled. FIG. 10 shows the $\Delta R/R_{end}$ of S2 upon exposure to 5% and 40% REI at different voltages between the electrodes contacting the NTMBT-AuNP film. As seen in the figure, the different voltages yielded different $\Delta R/R_{end}$ upon exposure to 40% RH, while there was no voltage effect on the $\Delta R/R_{end}$ upon exposure to 5% RH. These results comply with the presence of hysteresis only at high humidity levels. Applied rising voltages between 1 V to 5 V under 40% RH produced negative responses with rising magnitude, whereas an applied voltage of 0.9 V produced a positive response. Without being bound by any theory or mechanism of action, the positive response that was obtained below 0.9 V applied voltage indicates the presence of swelling mechanism and the absence of ionization mechanism. When applying voltages larger than 0.9 V, a reduction in resistance occurred (negative response). The higher the applied voltage, the larger the magnitude of the negative responses. Without being bound by any theory or mechanism of action, this observation indicates that the higher the applied voltage, above a specific voltage threshold, the more significant the role of the ionization and ionic current mechanisms. Because the swelling is an additive mechanism with respect to different VOCs and water (Konivalina Hoick, ACS Appl. Mater. Interf. 2012, 4, 317) the subtraction of the VOCs response from the water response would allow mathematical separation of the effect of water from other VOCs in the sample on the MCNP-based chemiresistor. These results provide an additional degree of freedom to deliberately control the MCNP sensing properties in real confounding environments with high and fluctuating levels of humidity as well as fouling nonspecific bindings. It is contemplated that the ionic conduction mechanism in MCNP sensors is affected by the humidity level and the applied voltage.

Figure 11:
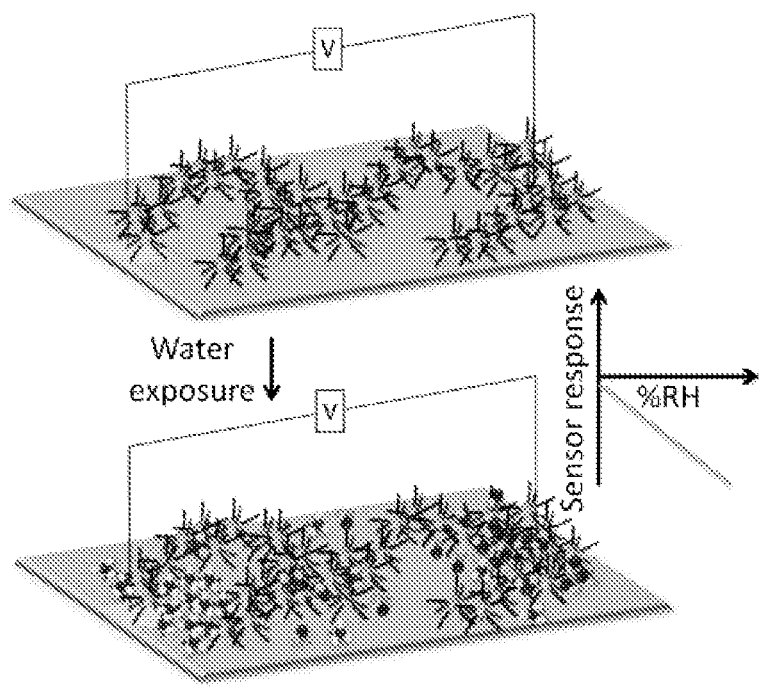
FIG. 11. A schematic representation of the response of monolayer-capped metallic nanoparticle (MCNP) chemiresistors on a $SiO_2$ substrate to volatile organic compounds (VOCs) and water vapor.
Figure 12:
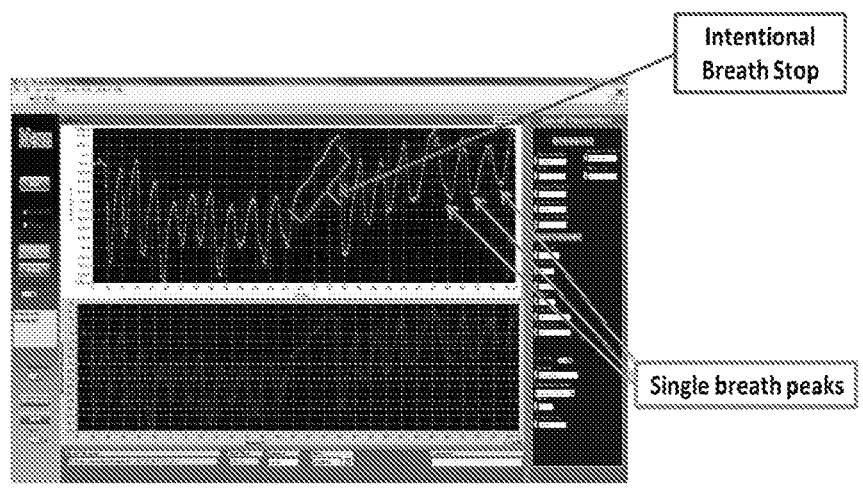
FIG. 12. Resistance vs. time of NTMBT-AuNPs in a single breath cycle.

Hence, the response of monolayer-capped metallic nanoparticle (MCNP) chemiresistors of the present invention to volatile organic compounds (VOCs) and water vapor can be engineered via systematic control of the MCNP film coverage (FIG. 11). The sensor of the present invention can thus be used for breath analysis, breath humidity sensing and breath monitoring. The fast response and return (recovery) time of the sensor enable its use as a breath switch which provides a detectable change in resistance upon breathing on the sensor (FIG. 12).

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method for detecting an analyte selected from a volatile organic compound (VOC), water vapor and combinations thereof in a subject's breath or in a sample, the method comprising the steps of:
   providing a sensor comprising a discontinuous film of conductive metallic nanoparticles capped with an organic coating on a substrate, the discontinuous film being interrupted by voids in coverage on the substrate that are free from the conductive metallic nanoparticles, wherein the voids range in size between 10-500 nm, permitting ionic conduction through condensate water vapor in the voids;
   providing a positive response upon exposure of the sensor to VOCs and a negative response upon exposure of the sensor to water vapor, wherein the positive response is an increase above a baseline and the negative response is a decrease below the baseline, and wherein the negative response is larger magnitude than the positive response;
   exposing the sensor to the subject's breath comprising said analyte or to said sample comprising said analyte; and
   detecting a signal generated from said analyte being exposed to the sensor.

2. The method according to claim 1, comprising detecting VOCs while concurrently determining an amount of water vapor, the method comprising the steps of:
   determining a contribution of water vapor in the detected signal; and
   extracting the contribution of water vapor from the detected signal thereby detecting VOCs in the subject's breath or in said sample.

3. The method according to claim 2, comprising applying a voltage to said sensor, and wherein the signal is detected at different applied voltages.

4. The method according to claim 3, comprising detecting VOCs in the subject's breath, wherein a detected level of VOCs is indicative of the presence of disease in the subject.

5. The method according to claim 1, comprising monitoring breathing of the subject, and comprising detecting the signal generated by water vapor present in the subject's breath.

6. The method according to claim 1, comprising monitoring a signal generated by water vapor present in breathing of the subject over time to obtain a respiratory waveform of the breathing of the subject.

7. The method according to claim 1, comprising activating an input device by detecting a signal generated by water vapor present in the subject's breath, and changing a configuration of a switch by the detected signal generated by water vapor present in the subject's breath to activate said input device.

8. A method of manufacturing a sensor comprising forming a discontinuous film of conductive metallic nanoparticles capped with an organic coating on a substrate, the discontinuous film being interrupted by voids in coverage on the substrate that are free from the conductive metallic nanoparticles, wherein the voids range in size between 10-500 nm, permitting ionic conduction through condensate water vapor in the voids, such that a positive response is provided upon exposure of the sensor to volatile organic compounds and a negative response is provided upon exposure of the sensor to water vapor, wherein the positive response is an increase above a baseline and the negative response is a decrease below the baseline, and wherein the negative response is larger magnitude than the positive response; and
   forming a continuous film of conductive metallic nanoparticles capped with an organic coating on the substrate adjacent the discontinuous film.

* * * * *